(12) United States Patent
Tanaka

(10) Patent No.: US 10,526,423 B2
(45) Date of Patent: Jan. 7, 2020

(54) EGGSHELL MEMBRANE SOLUBILIZATION METHOD USING ENZYMES

(75) Inventor: Shun-ichi Tanaka, Kakamigahara (JP)

(73) Assignee: AMANO ENZYME INC., Nagoya-shi (JP)

( * ) Notice: Subject to any disclaimer, the term of this patent is extended or adjusted under 35 U.S.C. 154(b) by 0 days.

(21) Appl. No.: 13/819,562

(22) PCT Filed: Aug. 12, 2011

(86) PCT No.: PCT/JP2011/068418
§ 371 (c)(1),
(2), (4) Date: Feb. 27, 2013

(87) PCT Pub. No.: WO2012/029529
PCT Pub. Date: Mar. 8, 2012

(65) Prior Publication Data
US 2013/0224830 A1     Aug. 29, 2013

(30) Foreign Application Priority Data
Aug. 31, 2010   (JP) .................................. 2010-195076

(51) Int. Cl.
C08B 37/08    (2006.01)
C08B 37/00    (2006.01)
C12N 9/06     (2006.01)

(52) U.S. Cl.
CPC ...... *C08B 37/0072* (2013.01); *C08B 37/0063* (2013.01); *C08B 37/0069* (2013.01); *C12N 9/0022* (2013.01)

(58) Field of Classification Search
CPC .... A61K 2300/00; A61K 38/00; A61K 45/06; A61K 35/57; A61K 8/981; C07K 14/465
See application file for complete search history.

(56) References Cited

U.S. PATENT DOCUMENTS

2007/0178170 A1    8/2007   Devore

FOREIGN PATENT DOCUMENTS

| JP | 04-148649 A | 5/1992 |
|----|-------------|--------|
| JP | 06-254149 A | 9/1994 |
| JP | H06-254149 A | 9/1994 |
| JP | 09-040564 A | 2/1997 |

(Continued)

OTHER PUBLICATIONS

Scott et al., Proc. Natl. Acad. Sci. USA 89: 658-662 (1992).*

(Continued)

*Primary Examiner* — Erin M. Bowers
(74) *Attorney, Agent, or Firm* — Locke Lord LLP

(57) ABSTRACT

The present invention addresses the problem of providing an eggshell membrane solubilization method that is capable of solving the problems associated with carrying out treatment using acids and alkalis, or problems associated with the processing methods of the conventional art that use proteases; in other words, an eggshell membrane solubilization method that is capable of solving at least one of the following problems: (1) the need for pretreatment such as pulverization, sonication or boiling; (2) the need for prolonged treatment; and (3) a low decomposition rate (approximately 20%). Eggshell membranes are efficiently solubilized by using a protease in combination with a reducing agent.

11 Claims, 27 Drawing Sheets

(56) References Cited

FOREIGN PATENT DOCUMENTS

| JP | 09-040664 | * | 2/1997 |
|---|---|---|---|
| JP | 09040664 | * | 2/1997 |
| JP | H09(1997)-224696 A | | 9/1997 |
| JP | 2002-253223 A | | 9/2002 |
| JP | 2003-506093 A | | 2/2003 |
| JP | 2008-007419 A | | 1/2008 |
| JP | 2008-007419 A | | 1/2008 |
| JP | 2008-061514 A | | 3/2008 |
| JP | 2008-118887 A | | 5/2008 |
| JP | 2008-289370 A | | 12/2008 |

OTHER PUBLICATIONS

Worthington, http://web.archive.org/web/20080820212829/http://www.worthington-biochem.com/PAP/PAP.pdf (archived Aug. 20, 2008, accessed Jul. 15, 2015).*

Asquith et al., Textile Research Journal 36(12): 1064-1071 (1966).*

Wolfram et al., Textile Research Journal 36(11): 947-953 (1966).*

Takahashi et al., Biosci. Biotech. Biochem. 60(8): 1299-1302 (1996).*

Bailey et al., J. Biol. Chem. 234: 1733-1739 (1959).*

Ahlborn et al., Protein J. 25(1): 71-81 (2006).*

Canfield, R. E.,"The Amino Acid Sequence of Egg White Lysozyme," J. Biol. Chem., 1963, vol. 238, No. 8, pp. 2698-2707.

Wu, Y. et al., "Characterization and developmental expression of chick aortic lysyl oxidase," J. Biol. Chem., 1992, vol. 267, No. 34, pp. 24199-24206.

Takahashi, K. et al., "Soluble egg shell membrane protein as a regulating material for collagen matrix reconstruction," Biosci. Biotechnol. Biochem.,1996, vol. 60, No. 8, pp. 1299-1302.

International Search Report dated Oct. 11, 2011, issued for PCT/JP2011/068418.

European Search Report and Opinion for European Application No. 11821547.4, dated Nov. 24, 2015.

Akagawa M. et al.: "Lysyl oxidase coupled with catalase in egg shell membrane", Biochimica et biophysica acta. Protein Structure and Molecular Enzymology, Elsevier, Amsterdam; NL, vol. 1434, No. 1, Sep. 14, 1999 (Sep. 14, 1999), pp. 151-160, XP004278783, ISSN: 0167-4838, DOI: 10.1016/S0167-4838(99)00169-7.

Hincke MT et al: "Identification and localization of lysozyme as a component of eggshell membranes and eggshell matrix", Matrix Biology, vol. 19, 2000, pp. 443-453, XP055228757.

Nakano T et al. "Extraction of Glycosaminoglycans form Chicken Eggshell", Poultry Science, 80, Jan. 1, 2001 (Jan. 1, 2001), pp. 681-684, XP055228657.

Takahashi et al.: "Soluble egg shell membrane protein as a regulating material for collagen matrix reconstruction", Biosci. Biotechnol. Biochem., vol. 60, No. 8, 1996, pp. 1299-1302, XP055081898.

Bailey JL et al.: "Studies on the Reaction of Sulfite with Proteins", The Journal of Biological Chemistry, 234(7), Jan. 1, 1959, pp. 1733-1739, XP055228779.

Japanese Decision of Refusal dated Feb. 26, 2016, JP2012-531781.

Yi et al., Macromol Biosci (2003) vol. 3, No. 5, p. 234-2378.

Ahlborn et al., Protein J. (2006) vol. 25, No. 1, p. 71-81.

Bailey et al., J. Biol. Chem. (1959) vol. 234, No. 7, p. 1733-1739.

* cited by examiner

[FIG. 1]
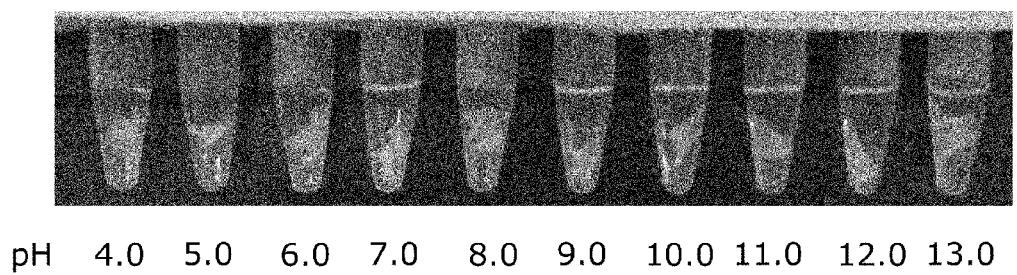

[FIG. 2]
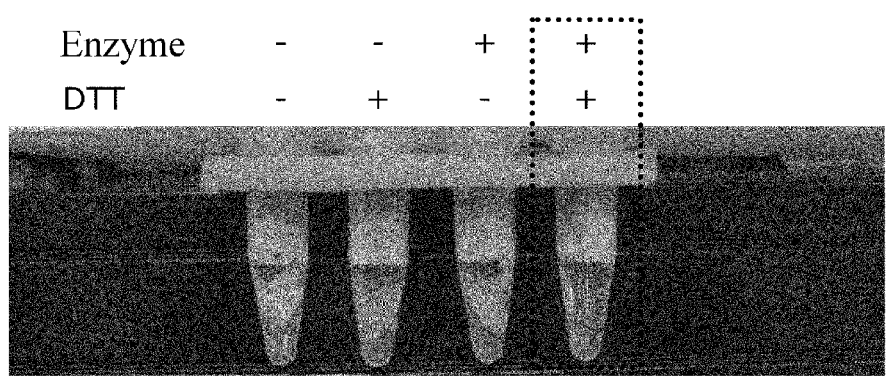

[FIG. 3]

| | Reducing agent | Solubilization of eggshell membranes | Enzyme conc. | Reaction time |
|---|---|---|---|---|
| Food additive | Sodium sulfite | ○ | 0.1% | 12 hours |
| | Sodium hydrogensulfite | ○ | 0.1% | 12 hours |
| | L-ascorbic acid (vitamin C) | × | 0.1% | 12 hours |
| | L-cysteine hydrochloride | ○ | 0.5% | 6 hours |
| | Sodium nitrite | × | 0.1% | 12 hours |
| | Sodium nitrate | × | 0.1% | 12 hours |
| | HITHION EXTRACT YH-8 | ○ | 0.5% | 6 hours |
| | HITHION EXTRACT YH-15 | ○ | 0.5% | 6 hours |
| | HITHION EXTRACT YH-D12 | × | 0.5% | 6 hours |
| | L-cysteine | ○ | 0.5% | 6 hours |
| | Glutathione | ○ | 0.5% | 6 hours |
| | DTT | ○ | 0.1% | 12 hours |
| | Sodium borohydride | × | 0.1% | 12 hours |

[FIG. 4]

[FIG. 5]
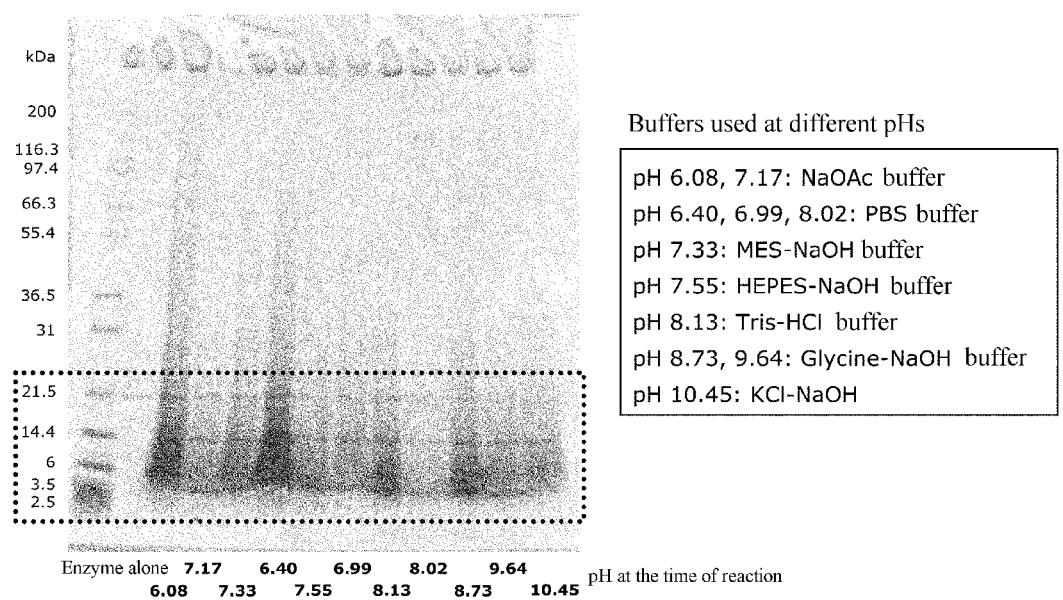

[FIG. 6]
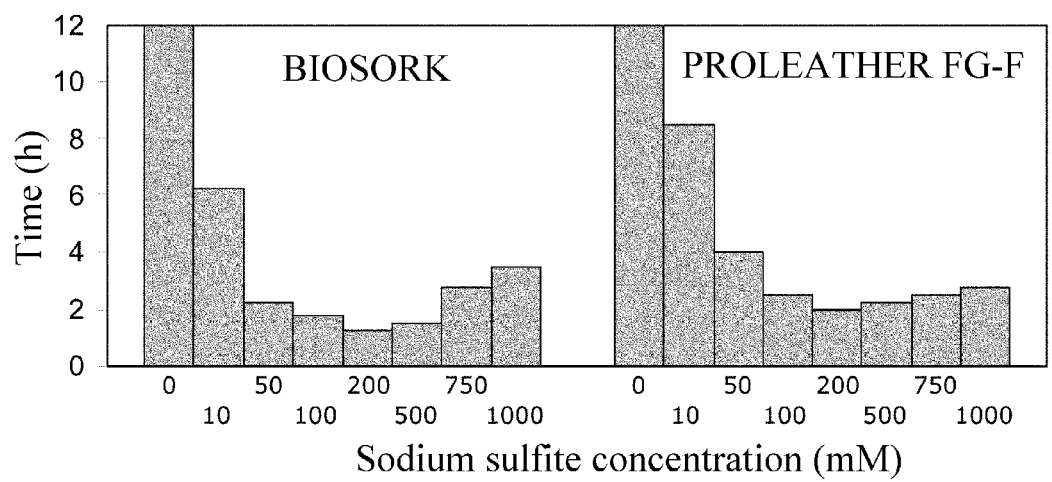

[FIG. 7]
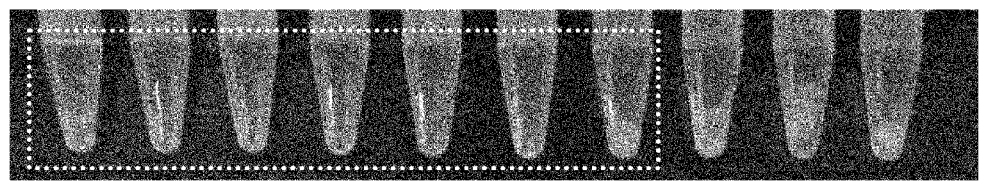

[FIG. 8]
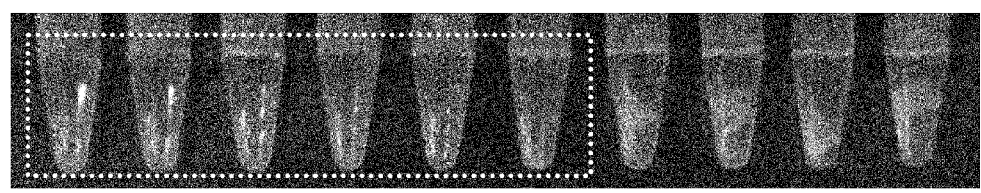

[FIG. 9]
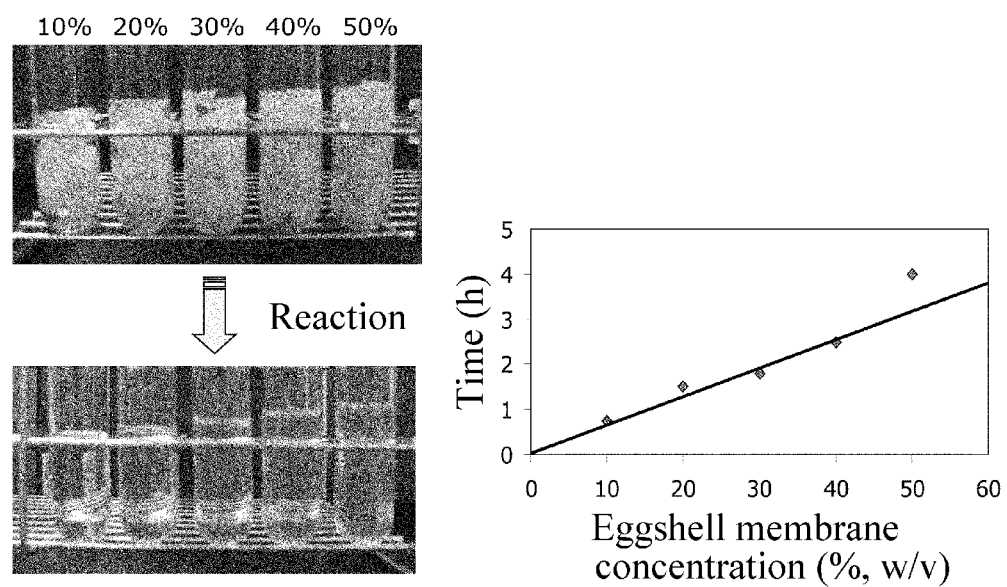

[FIG. 10]
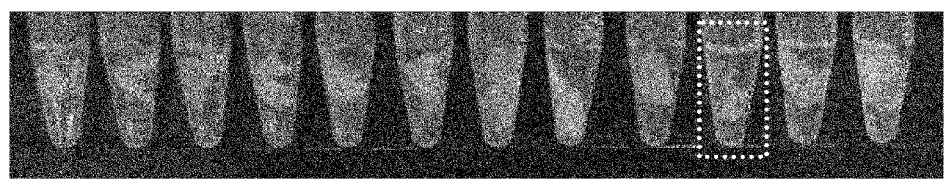

[FIG. 11]
| Na$_2$SO$_3$ | - | - | - | + | + | + | - | - | - | + | + | + |
| Enzyme | - | - | - | - | - | - | + | + | + | + | + | + |
| pH | 4.5 | 7.0 | 9.0 | 4.7 | 7.5 | 8.7 | 4.5 | 7.0 | 9.0 | 4.7 | 7.5 | 8.7 |

[FIG. 12]
| | | | | | | | | | | | | |
|---|---|---|---|---|---|---|---|---|---|---|---|---|
| Na$_2$SO$_3$ | - | - | - | + | + | + | - | - | - | + | + | + |
| Enzyme | - | - | - | - | - | - | + | + | + | + | + | + |
| pH | 4.5 | 7.0 | 9.0 | 4.7 | 7.5 | 8.7 | 4.5 | 7.0 | 9.0 | 4.7 | 7.5 | 8.7 |
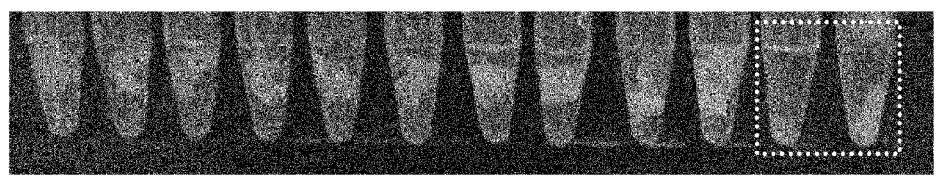

[FIG. 13]
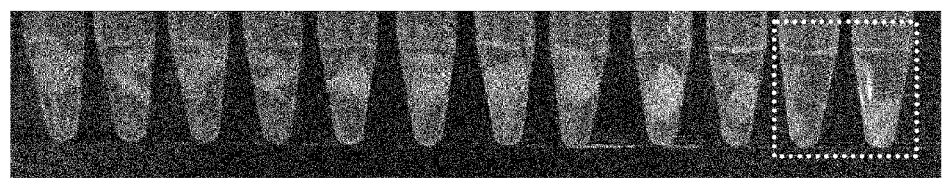

[FIG. 14]
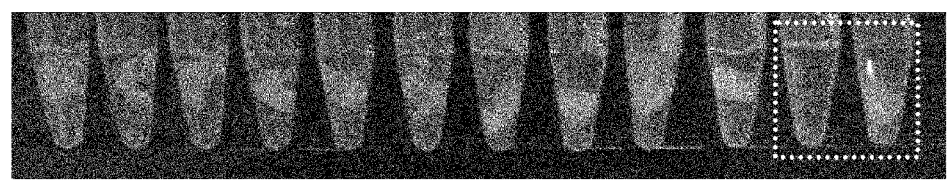

[FIG. 15]

[FIG. 16]
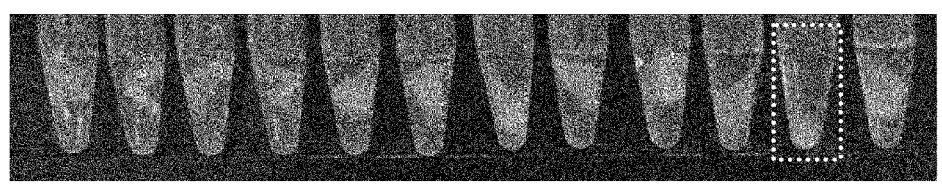

[FIG. 17]
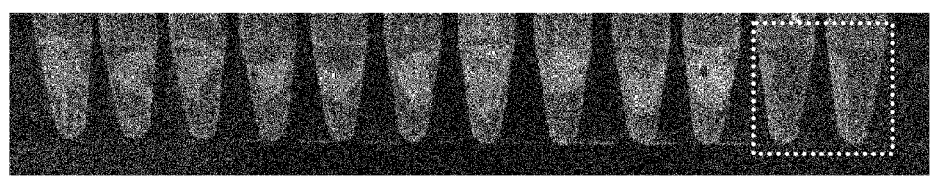

[FIG. 18]
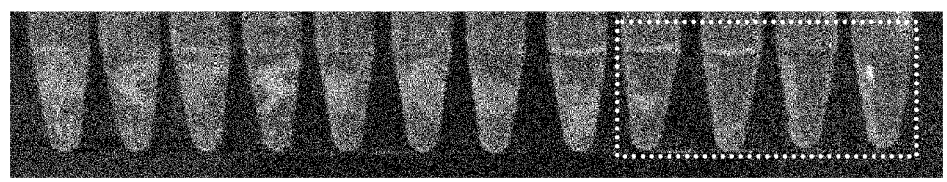

[FIG. 19]
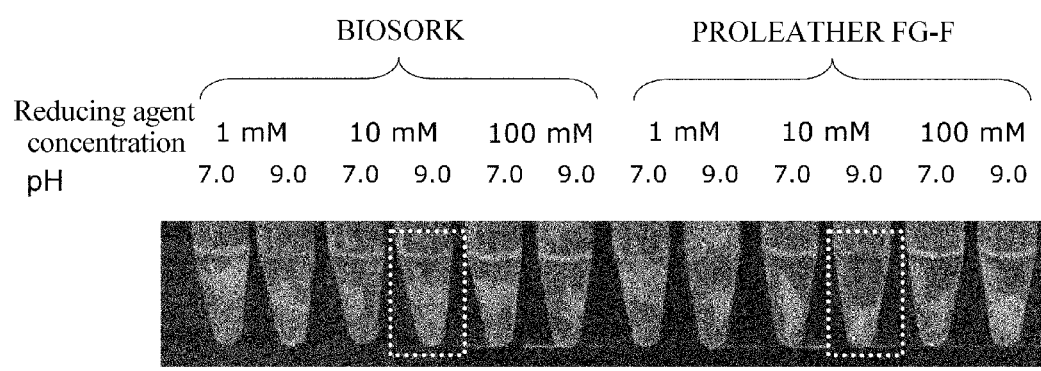

[FIG. 20]
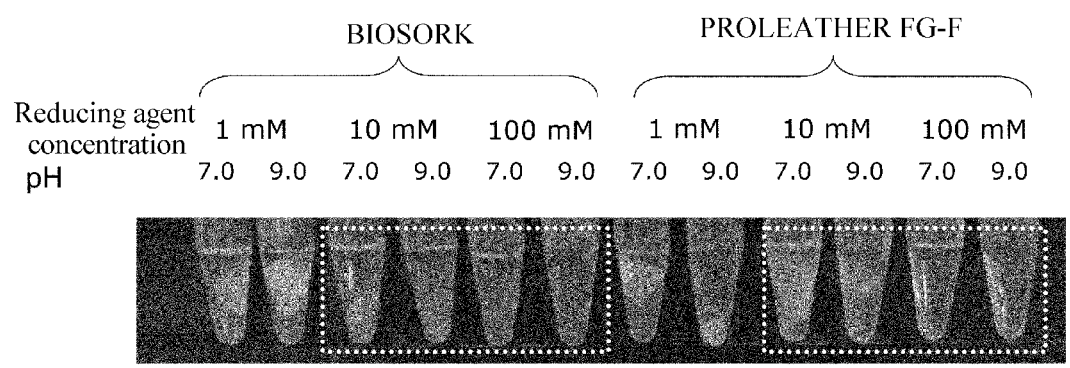

[FIG. 21]

| Sample | Sulfated GAG content (%) |
|---|---|
| Proteinase K decomposition product | 0.53 |
| BIOSORK decomposition product | 5.4 |
| PROLEATHER FG-F decomposition product | 1.1 |
| PAPAIN W40 decomposition product | 3.6 |

[FIG. 22]

| Sample | Hyaluronic acid content (%) |
|---|---|
| Proteinase K decomposition product | 0.11 |
| BIOSORK decomposition product | 0.043 |
| PROLEATHER FG-F decomposition product | 0.065 |
| PAPAIN W40 decomposition product | 0.026 |

[FIG. 23]
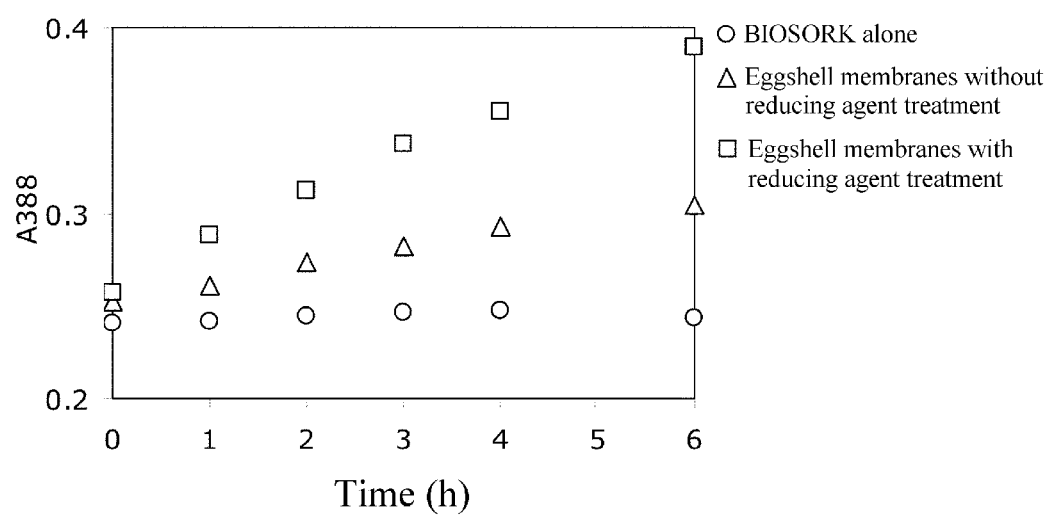

[FIG. 24]
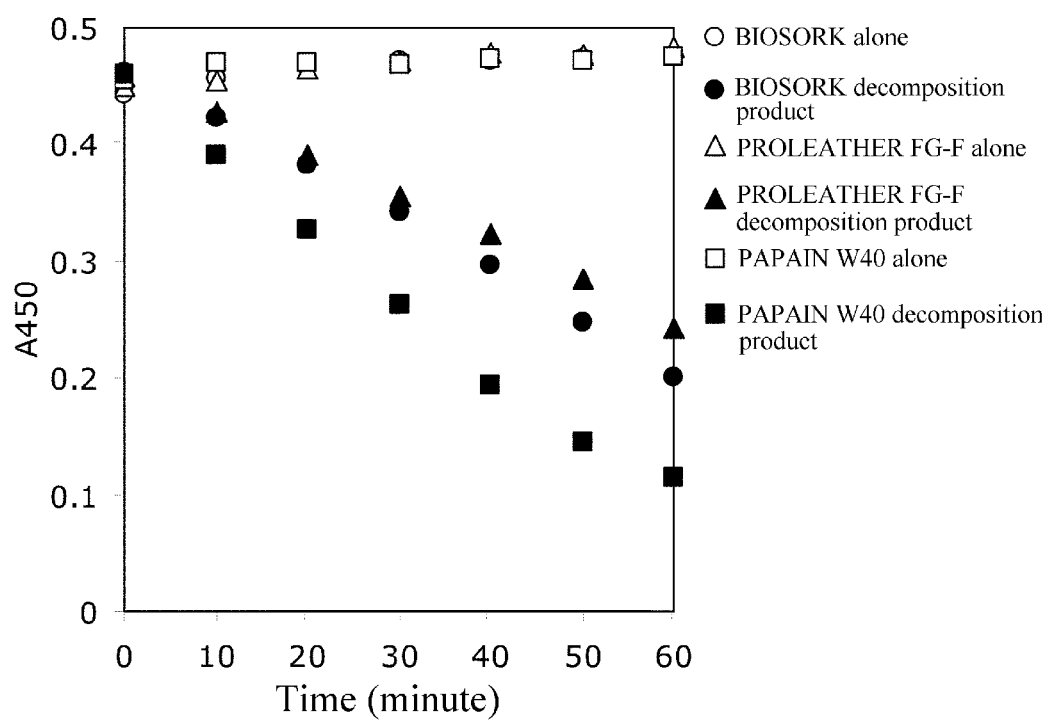

[FIG. 25]

| Sample | Antioxidative activity (μmol Trolox equivalent/100g) |
|---|---|
| BIOSORK decomposition product | 678.3 |
| PROLEATHER FG-F decomposition product | 521.7 |
| PAPAIN W40 decomposition product | 415.2 |

[FIG. 26]

| Sample | Antioxidative activity (µmol/L) |
|---|---|
| BIOSORK decomposition product | 3617.1 |
| PROLEATHER FG-F decomposition product | 2090.8 |
| PAPAIN W40 decomposition product | 2816.8 |

[FIG. 27]

| Sample | ACE inhibition rate (%) |
|---|---|
| BIOSORK decomposition product | 72.4 |
| PROLEATHER FG-F decomposition product | 74.5 |
| PAPAIN W40 decomposition product | 63.6 |

EGGSHELL MEMBRANE SOLUBILIZATION METHOD USING ENZYMES

TECHNICAL FIELD

The present invention relates to a method for solubilizing eggshell membranes using an enzyme, and specifically to a method for solubilizing eggshell membranes using a protease, and uses thereof. The present application claims priority based on Japanese Patent Application No. 2010-195076 filed on Aug. 31, 2010, and the content of the patent application is hereby incorporated by reference herein in its entirety.

BACKGROUND ART

The annual domestic consumptions of chicken and chicken eggs are reported to be as high as 2,200,000 tons and 2,500,000 tons, respectively. The worldwide consumptions of chicken and chicken eggs are about 83,000,000 tons and about 56,000,000 tons, respectively. On the other hand, inedible feathers and eggshell membranes are discharged in large amounts. Protein makes up 90% or more of feathers and eggshell membranes. The main component of feathers is keratin protein, and that of eggshell membranes is collagen-like protein. Both of them contain much cysteine (about 10%), and their decomposition products are known to have many physiological functions such as antioxidative action.

An eggshell membrane covers an egg cell (egg yolk) and an egg white in a chicken egg, and physically isolates them from the outside world together with the egg shell, thereby protecting the chicken egg from harmful ultraviolet rays, oxygen, and drying. In addition, eggshell membranes have an important function of protecting egg yolk and white from infection by adventives such as germs and viruses. In addition, eggshell membranes contain antibacterial substances and antibacterial enzymes such as lysozyme and β-N-acetylglucosaminidase. Eggshell membranes are also reported to contain other special proteins, and thus its functionality is receiving attention.

Various functional products containing eggshell membranes are known. Examples of the known products include a hair permanent agent containing eggshell membranes for protecting hair cuticle (Japanese Unexamined Patent Application Publication No. 2000-128744) and a court plaster containing an eggshell membrane decomposition product for wound healing (Japanese Unexamined Patent Application Publication No. 2003-225298).

Most parts of eggshell membranes are disposed of without use. The reason for this is that eggshell membranes are refractory and thus difficult to handle, and that there is no effective method for solubilizing eggshell membranes. At present, eggshell membranes are mainly treated by an acid or alkali, but this technique presents the problems of reddish browning color and development of malodor caused by amino acid decomposition. In addition, the yield of useful components is low because of excess reaction. As an alternative technique, protease treatment is studied (for example, see Patent Documents 1 to 4), but this technique is associated with the problems such as that (1) pretreatment processes such as pulverization, ultrasonication, and boiling are necessary, (2) long treatment is necessary, and (3) the decomposition rate is low (about 20%). The enzyme reaction proceeds under relatively mild conditions, so that the increase of the yield of active components is expected, but there is still no practical technique because of the above-described problems.

PRIOR ART DOCUMENTS

Patent Documents

Patent Document 1: Japanese Unexamined Patent Application Publication No. 2008-118887
Patent Document 2: Japanese Unexamined Patent Application Publication No. 2008-061514
Patent Document 3: Japanese Unexamined Patent Application Publication No. 09-040564
Patent Document 4: Japanese Unexamined Patent Application Publication No. 2008-007419

SUMMARY OF THE INVENTION

Problems to be Solved by the Invention

Accordingly, the present invention is intended to provide a method for solubilizing eggshell membranes and uses thereof, the method solves at least one of the above-described problems with prior art treatment methods (acid or alkali treatment and protease treatment).

Means for Solving Problem

In order to solve the above-described problems, the inventors continued dedicated research. As a result of this, they have found that eggshell membranes are solubilized very efficiently through the use of the combination of a protease and a reducing agent, particularly through the action of a protease in the presence of a reducing agent. It is surprising that complete solubilization, which is difficult by the prior art methods using an enzyme, was achieved by this method, and sufficient solubilization was achieved by an acidic protease, neutral protease, or alkaline protease, in spite of the fact that the process was carried out under mild pH conditions. As a result of further study, various conditions suitable for the solubilization were successfully identified. In addition, the study of the properties of the solubilized eggshell membranes obtained by the present method proved that the membranes contain useful substances, and that the solubilized product has a high utility value. Mainly on the basis of the above results, the present invention below has been accomplished.

[1] An eggshell membrane solubilization method using the combination of a protease and a reducing agent.

[2] The eggshell membrane solubilization method of [1], which comprises the step of subjecting eggshell membranes to the action of a protease in the presence of a reducing agent.

[3] The eggshell membrane solubilization method of [1], which comprises the following steps (1) and (2):
(1) a step of providing eggshell membranes in a solvent; and
(2) a step of adding a reducing agent and a protease to the solvent, and causing reactions by them.

[4] The eggshell membrane solubilization method of [3], wherein the pH of the reaction solution in the step (2) is from 4.5 to 9.5.

[5] The eggshell membrane solubilization method of [3] or [4], wherein the concentration of the reducing agent is from 5 mM to 1 M.

[6] The eggshell membrane solubilization method of any one of [3] to [5], wherein the reaction in the step (2) is continued until no solid is found.

[7] The eggshell membrane solubilization method of any one of [3] to [6], which further comprises the following step (3):

(3) a step of filtering the solution after the step (2), thereby removing solids.

[8] The eggshell membrane solubilization method of any one of [1] to [7], wherein the protease is an alkaline or neutral protease.

[9] The eggshell membrane solubilization method of any one of [1] to [7], wherein the protease is one or more enzymes selected from the group consisting of serine endopeptidases, cysteine endopeptidases, metalloendopeptidases, aminopeptidases, and aspartic endopeptidases.

[10] The eggshell membrane solubilization method of any one of [1] to [7], wherein the protease is one or more enzymes selected from the group consisting of chymotrypsin, subtilisin, papain, bacillolysin, stem bromelain, leucyl aminopeptidase, pepsin, and trypsin.

[11] The eggshell membrane solubilization method of any one of [1] to [7], wherein the protease is one or more enzymes selected from the group consisting of BIOSORK, PROLEATHER FG-F, PAPAIN W40, PROTEASE N, BROMELAIN F, UMAMIZYME G, THERMOASE Y100, PROTEAX, PROTEASE S, SUMIZYME LP500, DESKIN C, PROTIN NY10, PROTIN PC10, SUMIZYME MP, PROTIN AY, and PROTEINASE K.

[12] The eggshell membrane solubilization method of any one of [1] to [11],
wherein the reducing agent is one or more reducing agents selected from the group consisting of sulfites, hydrogensulfites, L-cysteine, N-acetyl-L-cysteine, 2-mercaptoethanol, glutathione, and DTT.

[13] The eggshell membrane solubilization method of any one of [1] to [11], wherein the reducing agent is sodium sulfite or sodium hydrogensulfite.

[14] The eggshell membrane solubilization method of [1], which includes the following steps (1) and (2'):

(1) a step of providing eggshell membranes in a solvent; and (2') a step of adding a reducing agent to the solvent to cause reaction, removing the reducing agent, and then adding a protease to cause its reaction.

[15] An eggshell membrane solubilizing agent using the combination of a protease and a reducing agent.

[16] The eggshell membrane solubilizing agent of [15], which includes a protease and a reducing agent.

[17] The eggshell membrane solubilizing agent of [15], which is a kit composed of a first component containing a protease and a second component containing a reducing agent.

[18] Solubilized eggshell membranes obtained by the eggshell membrane solubilization method of any one of [1] to [13].

[19] The solubilized eggshell membranes of [18], which includes one or more components selected from the group consisting of lysozyme, β-N-acetylglucosaminidase, hyaluronic acid, chondroitin sulfate, and dermatan sulfate.

[20] The solubilized eggshell membranes of [18], which exhibits one or more activities selected from the group consisting of antioxidative activity and angiotensin converting enzyme-inhibiting activity.

[21] Solubilized eggshell membranes obtained by the eggshell membrane solubilization method of [14].

[22] The solubilized eggshell membranes of [21], which includes lysyl oxidase.

[23] The solubilized eggshell membranes of any one of [18] to [22], which are completely solubilized eggshell membranes.

[24] A composition including the solubilized eggshell membranes of any one of [18] to [23].

[25] The composition of [24], which is a medicine, quasi-drug, food, or cosmetic.

[26] A method for extracting useful components from eggshell membranes, including the following steps (i) and (ii):

(i) a solubilization step according to the method of any one of [1] to [13]; and (ii) a step of purifying the solubilized eggshell membranes obtained by the solubilization step.

[27] The method of [26] for extracting useful components from eggshell membranes, wherein the component purified in the step (ii) is an enzyme selected from the group consisting of lysozyme and β-N-acetylglucosaminidase, or an acid mucopolysaccharide selected from the group consisting of hyaluronic acid, chondroitin sulfate, and dermatan sulfate.

[28] Lysozyme, β-N-acetylglucosaminidase, hyaluronic acid, chondroitin sulfate, or dermatan sulfate obtained by the method of [27].

[29] A method for extracting useful components from eggshell membranes, including the following steps (i') and (ii):

(i') a solubilization step according to the method of [14]; and (ii) a step of purifying the solubilized eggshell membranes obtained by the solubilization step.

[30] The method of [29] for extracting useful components from eggshell membranes, wherein the component purified in the step (ii) is lysyl oxidase.

[31] Lysyl oxidase obtained by the method of [30].

[32] An eggshell membrane extract obtained by the method of [26] or [29] for extracting useful components from eggshell membranes.

BRIEF DESCRIPTION OF THE DRAWINGS

FIG. 1 shows the result of decomposition of eggshell membranes using an enzyme preparation (BIOSORK) alone.

FIG. 2 shows the result of decomposition of eggshell membranes using an enzyme preparation (BIOSORK) and a reducing agent (DTT).

FIG. 3 is the table listing the type of the reducing agents tested and the presence or absence of occurrence of solubilization (decomposition) of eggshell membranes.

FIG. 4 is the graph showing the relationship between the pH conditions and the degree of solubilization when the enzyme preparation (BIOSORK) and reducing agent (sodium sulfite) were used in combination.

FIG. 5 shows the result of SDS-PAGE analysis of solubilized eggshell membranes.

FIG. 6 is the graph showing the dependence of solubilization of eggshell membranes on the reducing agent concentration. The left and right graphs show the results of the cases using BIOSORK and PROLEATHER FG-F, respectively.

FIG. 7 shows the solubilization of eggshell membranes using sodium sulfite and BIOSORK.

FIG. 8 shows the solubilization of eggshell membranes using sodium sulfite and PROLEATHER FG-F.

FIG. 9 shows the relationship between the eggshell membrane concentration and the solubilization time. The left shows the condition of the eggshell membranes before and after reaction. The right is the graph plotting the time required for complete solubilization of eggshell membranes at different concentrations.

FIG. 10 shows the solubilization of eggshell membranes using pepsin and a reducing agent in combination.

FIG. 11 shows the solubilization of eggshell membranes using SUMIZYME LP500 and a reducing agent in combination.

FIG. 12 shows the solubilization of eggshell membranes using DESKIN C and a reducing agent in combination.

FIG. 13 shows the solubilization of eggshell membranes using PROTIN NY10 and a reducing agent in combination.

FIG. 14 shows the solubilization of eggshell membranes using PROTIN PC10 and a reducing agent in combination.

FIG. 15 shows the solubilization of eggshell membranes using TRYPSIN and a reducing agent in combination.

FIG. 16 shows the solubilization of eggshell membranes using SUMIZYME MP and a reducing agent in combination.

FIG. 17 shows the solubilization of eggshell membranes using PROTIN AY and a reducing agent in combination.

FIG. 18 shows the solubilization of eggshell membranes using PROTEINASE K and a reducing agent in combination.

FIG. 19 shows the solubilization of eggshell membranes using N-acetyl-L-cysteine as a reducing agent.

FIG. 20 shows the solubilization of eggshell membranes using 2-mercaptoethanol as a reducing agent.

FIG. 21 is the table showing the sulfated glycosaminoglycan (GAG) content in the solubilized eggshell membranes.

FIG. 22 is the table showing the hyaluronic acid content in the solubilized eggshell membranes.

FIG. 23 is the graph showing the lysyl oxidase activity of the solubilized eggshell membranes.

FIG. 24 is the graph showing the bacteriolysis activity of the solubilized eggshell membranes.

FIG. 25 is the graph showing the free radical scavenging activity of the solubilized eggshell membranes.

FIG. 26 is the graph showing the $Cu^{2+}$ reducing activity of the solubilized eggshell membranes.

FIG. 27 is the graph showing the angiotensin converting enzyme (ACE) inhibition rate by the solubilized eggshell membranes.

DETAILED DESCRIPTION OF THE INVENTION

1. Eggshell Membrane Solubilization Method

A first aspect of the present invention relates to an eggshell membrane solubilization method. According to the method of the present invention, eggshell membranes are efficiently solubilized with avoiding problems of reddish browning coloring and development of malodor caused by amino acid decomposition. In addition, a high solubilization (decomposition) rate is achieved without pretreatment.

In the present description, "eggshell membrane" means the membrane located at the inside of the outer shell of eggs of birds such as chicken, partridge, silky fowl, duck, goose, and ostrich. In the solubilization method of the present invention, eggshell membranes are solubilized through the treatment using the combination of a protease and a reducing agent. The state of the eggshell membranes to be treated is not particularly limited. For example, dry eggshell membranes prepared by separating the membranes from the outer shell, followed by drying (for example, solar drying, hot-air drying, vacuum drying, aspiration drying, or freeze drying), wet eggshell membranes before drying, or wet eggshell membranes prepared by swelling after drying may be used. Alternatively, the eggshell membranes may be shredded or pulverized (for example, powder). Yet alternatively, the eggshell membranes unseparated from the shell may be used.

In the present invention, "the combination of a protease and a reducing agent" means the treatment of eggshell membranes with a protease under the action of a reducing agent. The timing of the action of a protease on eggshell membranes and the timing of the use of a reducing agent are not particularly limited as long as the environment allowing the action of the reducing agent is formed. In a preferred manner, the actions of a reducing agent and a protease are exerted at the same time, thereby more efficiently solubilizing eggshell membranes. In a typical manner, eggshell membranes are subjected to the action of a protease in the presence of a reducing agent. In this embodiment, for example, the following steps (1) and (2) are carried out:

(1) a step of providing eggshell membranes in a solvent; and (2) a step of adding a reducing agent and a protease to the solvent, and causing reactions by them.

The solvent used in the step (1) is not particularly limited as long as enzyme reaction occurs, but is preferably a buffer solution, thereby facilitating pH adjustment and maintenance of desired pH. In the step (2), the timing and order of addition of the reducing agent and protease are not particularly limited. In a preferred manner, the reducing agent and protease are added at the same time, or the protease is added after (preferably immediately after) the addition of the reducing agent, thereby sufficiently achieving the combination effect. The former method is advantageous in terms of easiness of operation, because the addition operation is performed only once.

Different from the above-described embodiment, the eggshell membranes after treatment with a reducing agent may be subjected to the action of a protease. In this embodiment, for example, the following steps (1) and (2') are carried out; this embodiment is particularly suitable for obtaining solubilized eggshell membranes containing lysyl oxidase having activity:

(1) a step of providing eggshell membranes in a solvent; and (2') a step of adding a reducing agent to the solvent to cause reaction, removing the reducing agent, and then adding a protease to cause its reaction.

The protease used in the present invention is not particularly limited as long as it achieves efficient solubilization of eggshell membranes. The protease may be a commercially available enzyme preparation. Examples of the enzyme preparation include BIOSORK, NEWLASE F3-G, NEWLASE A, protease A "AMANO" G, PROTEASE N "AMANO" G, PROTEASE S "AMANO" G, PAPAIN W-40, BROMELAIN F, PROTIN NY10, PROTIN PC10, PROTIN AY, PROTIN SD-NY10, PROTIN SD-PC10F, THERMOASE PC10F, PROTIN SD-AC10F, PROTIN SD-AY10, PROLEATHER FG-F, PROTEASE P "AMANO" 3G, PROTEASE M "AMANO" G, and PROTEAX (Amano Enzyme Inc.), MOLSIN F (Kikkoman Food Products Company), SUMIZYME AP, SUMIZYME LP, SUMIZYME LP500, SUMIZYME FP, SUMIZYME LPL, SUMIZYME MP (Shinnihon Chemicals Corporation), DENAPSIN 2P, DENATYME AP, BIOPRASE OP, BIOPRASE AL-15FG, BIOPRASE 30G, BIOPRASE APL-30, BIOPRASE OR-10G, BIOPRASE 30L, BIOPRASE XL-416F, BIOPRASE SP-20FG, BIOPRASE SP-4FG, and PROTEASE CL-15 (Nagase ChemteX Corporation), ORIENTASE 20A, TETRASE S, NUCLEICIN, ORIENTASE 10NL, ORIENTASE 90N, ORIENTASE ONS, and ORIENTASE 22BF (HBI Enzymes Inc.), BREWERS CLAREX, VARIDASE AFP, VARIDASE FP60, BREWERS PROTEASE, ACCELERZYME NP50.000, DELVOLASE, VARIDASE TSP200, BAKEZYME PPU95.000, BAKEZYME B500, COLLUPULINE, VARIDASE PAPAIN SF, and VARIDASE BROMELAIN (DSM Japan), PROTEASE YP-SS, PANTIDASE NP-2, PANTIDASE P, AROASE AP-10, AROASE NP-10, AROASE NS, AROASE XA-10, and PROTEASE AL (Yakult Pharmaceutical Industry Co., Ltd.), PROMOD 223LP, PROTEX 7L, PROTEX 14L, Alkaline Protease GL, PROTEX 6L, PROTEX 89L, PURAFECT, PURAFECT OX, PROPERASE, PROTEX OXG, and PROTEX 40L (Genencor Kyowa Co., Ltd.), PTN, NEWTRASE, ESPERASE, SAVINASE, ALCALASE, CLEARLENS PRO, EVERLASE, KANNASE, POLARZYME, FLAVOURZYME, PROTAMEX, and NOVOLAN (Novozymes Japan), PAPAIN F., TRYPSIN 4.0T, COROLASE N, VERON L10, COROLASE L10, COROLASE 7089, and VERON W (Higuchi Inc.), ENZYLON NBS, ENZYLON SA, and MAGNAX MT (Rakuto Kasei Industrial Co., Ltd.), KOKULASE P (Mitsubishi-Kagaku Foods Corporation), ACTINASE AS and ACTINASE AF (Kaken Pharma Co., Ltd.), GRINDAMYL PR59 and GRINDAMYL PR43 (Danisco Japan), SOFTERGEN M2 (Taisho Teclmos Co., Ltd.), PROTEINASE K (Wako Pure Chemical Industries, Ltd.), and DESKIN C (Daiwa Fine Chemicals Co., Ltd.).

As shown by the below-described examples, eggshell membranes were completely solubilized in a short time when BIOSORK, PROLEATHER FG-F, PAPAIN W40, PROTEASE N, BROMELAIN F, UMAMIZYME G, THERMOASE Y100, PROTEAX, or PROTEASE S was used. In addition, eggshell membranes were efficiently solubilized also when SUMIZYME LP500, DESKIN C, PROTIN NY10, PROTIN PC10, SUMIZYME MP, PROTIN AY, PROTEINASE K, PEPSIN, or TRYPSIN was used. On the basis of these results, in a preferred embodiment, one or more enzyme preparations selected from these enzyme preparations or enzymes are used as protease(s). Examples of the enzymes composing these enzyme preparations include chymotrypsin with an optimum pH in the alkaline range and classified as a serine endopeptidase, subtilisin with an optimum pH in the alkaline range and classified as a serine endopeptidase, papain with an optimum pH in the neutral range and classified as a cysteine endopeptidase, bacillolysin with an optimum pH in the neutral range and classified as a metalloendopeptidase, stem bromelain with an optimum pH in the neutral range and classified as a cysteine endopeptidase, and leucyl aminopeptidase with an optimum pH in the neutral range and classified as an aminopeptidase. Pepsin has an optimum pH in the acidic range and is classified as an aspartic endopeptidase, and trypsin has an optimum pH in the neutral range and is classified as a serine endopeptidase. On the basis of these facts, in a preferred embodiment of the present invention, one or more enzymes selected from the group consisting of serine endopeptidases, cysteine endopeptidases, metalloendopeptidases, aminopeptidases, and aspartic endopeptidases are used. More specifically, one or more enzymes selected from the group consisting of chymotrypsin, subtilisin, papain, bacillolysin, stem bromelain, leucyl aminopeptidase, pepsin and trypsin are used. On the other hand, on the basis of the fact that many alkaline proteases and neutral proteases achieved successful solubilization (see the below-described examples), in a preferred embodiment, an alkaline protease and a neutral protease are used.

As shown by the below-described examples, eggshell membranes were completely solubilized in a very short time when BIOSORK, PROLEATHER FG-F, or PAPAIN W40 was used. Accordingly, it is preferred that one or more of these enzyme preparations, or one or more of the enzymes composing these enzyme preparations (more specifically, chymotrypsin (a component of BIOSORK), subtilisin (a component of PROLEATHER FG-F), and papain (a component of PAPAIN W40)) are used as protease(s). In the most preferred embodiment, BIOSORK, which showed complete solubilization of eggshell membranes in the shortest time, or chymotrypsin composing BIOSORK is used as at least one protease.

The protease used in the present invention may not be a purified product. For example, a plant extract, an animal extract, a microbial culture extract, or a partially purified product of any of them may be used as a protease, as long as efficient solubilization of eggshell membranes is achieved.

Examples of the reducing agent include a sulfite and a hydrogensulfite. The salt is, for example, an alkali metal, alkaline earth metal, or ammonium salt (specifically, for example, sodium, potassium, or monoethanolamine). In a more preferred manner, a sulfite (for example, sodium sulfite) is used.

The reducing agent may be a thiol or a phosphine. Examples of the thiol include cysteine and its derivatives (for example, N-acetylcysteine), cysteamine and its derivatives (examples of the derivatives include C1-C4 acyl derivatives, more specifically N-acetylcysteamine and N-propionylcysteamine), thiolactic acid and its esters (examples of the esters of thiolactic acid include glycerol monothiolactate), thioglycolic acid and its esters (examples of the esters of thioglycolic acid include glycerol and glycol monothioglycolates), and thioglycerol and its mixtures. Specific examples of the thiols include N-mercaptoalkylamides, N-(mercaptoalkyl)-ω-hydroxyalkyl amides, N-mono- or N,N-dialkylmercapto-4-butylamides, aminomercaptoalkylamides, alkylaminomercaptoalkylamides, and 2-mercaptoethanol. Examples of the N-mercaptoalkylamides include N-(mercapto-2-ethyl)gluconamide, β-mercaptopropionic acid and its derivatives, thiomalic acid, and pantetheine. Examples of the N-(mercaptoalkyl)-ω-hydroxyalkylamides include those described in Japanese Unexamined Patent Application Publication No. 2-104515. Examples of the N-mono- or N,N-dialkylmercapto-4-butylamides include those described in Japanese Unexamined Patent Application Publication No. 2-196711. Examples of the aminomercaptoalkylamides include those described in Japanese Unexamined Patent Application Publication No. 3-170411. Examples of the alkylaminomercaptoalkylamides include those described in Japanese Unexamined Patent Application Publication No. 5-279322.

Examples of the phosphine include tri(hydroxymethyl)phosphine, tri(hydroxypropyl)phosphine, bis(hydroxymethyl)(phenyl)phosphine, allyldiphenylphosphine, benzyldiphenylphosphine, bis(3,4,5-trimethoxyphenyl)chlorophosphine, bis(3,4,5-trimethoxyphenyl)phosphine, benzyloxy(diisopropylamino)methylphosphine, bis(diisopropylamino)chlorophosphine, bis(2-cyanoethyl)phosphine, bis(3,5-di-tert-butylphenyl)chlorophosphine, bis(3,5-di-tert-butylphenyl)phosphine, bis(diethylamino)methylphosphine, bis(diethylamino)chlorophosphine, bis(diethylamino)phenylphosphine, bis(3,5-dimethyl-4-methoxyphenyl)chlorophosphine, bis(3,5-dimethyl-4-methoxyphenyl)phosphine, bis(3,5-dimethylphenyl)chlorophosphine, bis(3,5-dimethylphenyl)diethylaminophosphine, bis(3,5-dimethylphenyl)phosphine, bis(3,5-ditrifluoromethylphenyl)chlorophosphine, bis(3,5-ditrifluoromethylphenyl)phosphine, bis(4-fluorophenyl)chlorophosphine, bis(2-furyl)chlorophosphine, bis(2-furyl)phosphine, bis(hydroxymethyl)phenylphosphine, bis(4-methoxyphenyl)phenylphosphine, bis(3,5-dimethylphenyl)phosphine, bis(3,5-di-tert-butylphenyl)chlorophosphine, bis(3,5-di-tert-butylphenyl)phosphine, bis(3,5-ditrifluoromethylphenyl)chlorophosphine, bis(3,5-ditrifluoromethyl phenyl) phosphine, bis(4-fluorophenyl)chlorophosphine, bis(4-methoxyphenyl)chlorophosphine, bis(4-methoxyphenyl)phenylphosphine, bis(4-methylphenyl)chlorophosphine, bis(4-methylphenyl)phosphine, bis(4-trifluoromethylphenyl)chlorophosphine, bis(4-trifluoromethylphenyl)phosphine, bis(diethylamino)methylphosphine, bis(diethylamino)phenylphosphine, bis(hydroxymethyl)phenylphosphine, bis(o-tolyl)chlorophosphine, bis(o-tolyl)phosphine, bis(pyrrolidino)methylphosphine, butyldichlorophosphine, butyldiphenylphosphine, tert-butyldiphenylphosphine, cyclohexyl(diethylamino)chlorophosphine, cyclohexyl(dimethylamino)chlorophosphine, cyclohexyldichlorophosphine, cyclohexyldiphenylphosphine, 2-chloroethyldiphenylphosphine, 2-(dicyclohexylphosphino)biphenyl, 2-dicyclohexylphosphino-2'-(N,N-dimethylamino)biphenyl, diethylaminodiethylphosphine, dimethylaminodichlorophosphine, (4-dimethylaminophenyediphenylphosphine, N-[(diphenylphosphinyl)methyl]-N-methylaniline, o-diphenylphosphinobenzoic acid, 2-methoxy(dichlorophosphino) benzene, 4-methoxyphenyl(diethylamino)chlorophosphine, 4-methoxyphenyl(dimethylamino)chlorophosphine, (2-methoxyphenyl)methylphenylphosphine, 2-methoxyphosphinobenzene, (5-methyl-2-isopropyl cyclohexyl)diphenylphosphine, triphenylphosphine, diallylphenylphosphine, dibenzylphosphine, dibutylphenylphosphine, dibutylphosphine, dicyclohexylchlorophosphine, dicyclohexylphenylphosphine, dicyclohexylphosphine, diethylchlorophosphine, diethylphenylphosphine, diethylphosphine, diisobutylphosphine, diisopropylchlorophosphine, diisopropylphosphine, dimethyl(phenyl)phosphine, dimethyl(trimethylsilyl)phosphine, dimethylchlorophosphine, diphenyl(o-tolyl)phosphine, diphenyl(p-tolyl)phosphine, diphenyl(trimethylsilyl)phosphine, diphenylchlorophosphine, diphenylphosphine, diphenylpropylphosphine, diphenylvinylphosphine, di-tert-butylchlorophosphine, di-tert-butylhydroxy phosphine, di-tert-butyl methylphosphine, di-tert-butylphenylphosphine, di-tert-butylphosphine, divinylphenylphosphine, ethyldichlorophosphine, ethyldiphenylphosphine, isopropyldichlorophosphine, methoxydiethoxyphosphine, methyldichlorophosphine, methyldiphenylphosphine, methylphenylchlorophosphine, phenylphosphine, propyldichlorophosphine, tert-butyl-bis(trimethylsilyl)phosphine, tert-butyldichlorophosphine, tert-butyldiethylphosphine, tert-butyldiphenylphosphine, tert-butylphosphine, tri(m-tolyl)phosphine, tri(o-tolyl)phosphine, tri(p-tolyl)phosphine, tricyclohexyl phosphine, tricyclopentylphosphine, triethylphosphine, triisobutylphosphine, triisopropylphosphine, trimethylphosphine, tri-n-butyl phosphine, tri-n-octylphosphine, tripropylphosphine, tris(1-naphthyl)phosphine, tris(2,4,6-trimethylphenyl)phosphine, tris(2,6-dimethoxyphenyl)phosphine, tris(2-carboxyethyl)phosphine, tris(2-cyanoethyl)phosphine, tris(2-furyl)phosphine, tris(2-methoxy phenyl)phosphine, tris(2-triethyl)phosphine, tris(3,5-dimethyl-4-methoxy) phosphine, tris(3-chlorophenyl)phosphine, tris(3-fluorophenyl)phosphine, tris(3-methoxyphenyl)phosphine, tris(3-methoxypropyl)phosphine, tris(4-chlorophenyl)phosphine, tris(4-fluorophenyl)phosphine, tris(4-methoxyphenyl)phosphine, tris(4-morpholino)phosphine, tris(hydroxymethyl) phosphine, tris(trimethylsilyl)phosphine, tris[3,5-bis(trifluoromethyl)phenyl] phosphine, tri-tert-butyl phosphine, 2-cyanoethyl diphenyl phosphine, 2-dicyclohexylphosphino-2'-methylbiphenyl, bis(2,4,6-trimethylphenyl)phosphine, and 2-(di-tert-butylphosphino)biphenyl.

According to one preferred embodiment, a reducing agent which achieved successful solubilization (see the below-described examples), more specifically, a sulfite (for example, sodium sulfite), a hydrogensulfite (for example, sodium hydrogensulfite), L-cysteine, L-cysteine hydrochloride, N-acetyl-L-cysteine, 2-mercaptoethanol, glutathione (or a yeast extract containing glutathione), or DTT is used. Not to mention, two or more reducing agents may be used in combination, as long as the action and effect necessary for the present invention are achieved.

The reaction in the step (2) is preferably carried out under weakly acidic pH to weak alkaline pH conditions (specifically pH 4.5 to 9.5). More preferably, the reaction is carried out under neutral pH conditions. The neutral pH here means pH 6.0 to 8.0. In a preferred manner, the reaction is caused in a reaction liquid whose pH has been adjusted to 7.0 to 7.5.

The reaction time in the step (2) may be freely established in the range of, for example 10 minutes to 24 hours. According to the method of the present invention, efficient solubilization proceeds, so that eggshell membranes are solubilized in a short time. In a preferred manner, the reaction time is established so as to achieve complete solubilization of eggshell membranes. In order to improve the reaction efficiency, the reaction may be carried out under stirring or shaking.

The temperature conditions are not particularly limited, and may be established within the range which will not affect the action of the protease to be used. The temperature conditions are, for example, from 30° C. to 80° C., and preferably from 40° C. to 70° C.

The usage (loading) of a protease is not particularly limited as long as the protease allows efficient solubilization of eggshell membranes. The optimum usage of the protease usually depends on the type of enzyme to be used, and, for example, from 0.01% (W/W) to 20% (W/W) in terms of the concentration of the protease in the reaction liquid. The concentration of the protease in the reaction liquid is preferably from 0.1% (W/W) to 20% (W/W), and more preferably from 0.1% (W/W) to 10% (W/W).

The usage of a reducing agent is also not particularly limited as long as the effect of combination with the protease is sufficiently achieved. In general, the optimum usage depends on the type of the reducing agent to be used; for example, the reducing agent is used in an amount such that the concentration of the reducing agent in the reaction liquid is from 5 mM to 1 M. The concentration of the reducing agent in the reaction liquid is preferably from 10 mM to 500 mM, and more preferably from 50 mM to 500 mM.

The optimum conditions (for example, pH, reaction time, temperature, usage of enzyme, and usage of reducing agent) are readily established based on the result of preliminary experiment, in light of the teachings herein.

The above-described various conditions also applies to the reaction in the step (2').

As supported by the experimental results shown in the below-described examples, the method of the present invention allows complete solubilization of eggshell membranes, in spite of its simple operation. The "complete solubilization of eggshell membranes" means the decomposition of eggshell membranes until no solid is found by at least visual observation. In the method of the present invention, the "complete solubilization of eggshell membranes" is not essential, but establishment of conditions for achieving "complete solubilization of eggshell membranes" is preferred for extracting the useful components from eggshell membranes with minimum wastes, and for dispensing with the removal of residues. Therefore, in one aspect of the present invention, the reaction in the step (2) (or (2')) is continued until no solid is found. On the other hand, in another embodiment of the present invention, the step (2) (or (2')) is completed with the solid content remained, and then the solution is filtered, and the solid content is removed (step (3)). This embodiment is useful for, for example, obtaining easily decomposed or deactivated components.

2. Eggshell Membrane Solubilizing Agent

A second aspect of the present invention relates to an eggshell membrane solubilizing agent. The eggshell membrane solubilizing agent of the present invention is characterized by using a protease and a reducing agent in combination. In other words, the eggshell membrane solubilizing agent of the present invention uses the combination of a protease and a reducing agent. Typically, the eggshell membrane solubilizing agent of the present invention is provided as a formulation prepared by mixing a protease with a reducing agent. Alternatively, for example, the eggshell membrane solubilizing agent of the present invention may be provided in the form of a kit composed of an element containing a protease (first component) and another element containing a reducing agent (second component). Two or more proteases may be combined, and two or more reducing agents may be combined. The protease and reducing agent are the same as those used in the eggshell membrane solubilization method of the present invention, so that overlapping explanations thereof are omitted.

The eggshell membrane solubilizing agent of the present invention contains active components (a protease and/or a reducing agent), and may further contain, for example, an excipient, a buffer, a suspending agent, a stabilizer, a preservative, an antiseptic, a normal saline solution, and the like. Examples of the excipient include lactose, sorbitol, D-mannitol, and white sugar. Examples of the buffer include phosphates, citrates, and acetates. Examples of the stabilizer include propylene glycol and ascorbic acid. Examples of the preservative include phenol, benzalkonium chloride, benzyl alcohol, chlorobutanol, and methylparaben. Examples of the antiseptic include benzalkonium chloride, paraoxybenzoic acid, and chlorobutanol.

3. Solubilized Eggshell Membranes and Composition Containing the Same

Another aspect of the present invention provides solubilized eggshell membranes obtained by the eggshell membrane solubilization method. One preferred embodiment provides completely solubilized eggshell membranes. The eggshell membrane solubilization method of the present invention allows solubilization of eggshell membranes under mild conditions. Accordingly, the solubilized eggshell membranes obtained by this method are rich in useful components contained in eggshell membranes (for example, protein (including enzymes such as lysyl oxidase, lysozyme, and β-N-acetylglucosaminidase, and collagen protein), glycoprotein, peptide (including collagen peptide), glycopeptide, amino acids, and acid mucopolysaccharides such as hyaluronic acid, chondroitin sulfate, and dermatan sulfate). In one embodiment, the solubilized eggshell membranes obtained by the method of the present invention contain one or more components selected from the group consisting of lysozyme, β-N-acetylglucosaminidase, hyaluronic acid, chondroitin sulfate, and dermatan sulfate. The solubilized eggshell membranes obtained by the method of the present invention may be characterized in that they exhibit antioxidative activity and/or angiotensin converting enzyme-inhibiting activity. The solubilized eggshell membranes according to another embodiment are characterized in that they contain lysyl oxidase. The solubilized eggshell membranes containing lysyl oxidase are typically obtained by the eggshell membrane solubilization method including the steps (1) and (2').

The present invention also provides a composition containing solubilized eggshell membranes. The application of the composition of the present invention is not particularly limited, and preferred applications include medicines, quasi drugs, foods, and cosmetics. More specifically, a preferred embodiment of the present invention provides a pharmaceutical composition, a quasi drug composition, a food composition, and a cosmetic composition containing solubilized eggshell membranes. Examples of the application and effect of the pharmaceutical composition and quasi drug composition of the present invention include prevention of oxidation, inhibition of growth of bacteria, prevention of inflammation, wound healing, blood pressure lowering, hair fostering, and nutritional supplementation.

The pharmaceutical composition and quasi drug composition of the present invention may be formulated in accordance with a common procedure. The formulation may contain pharmaceutically acceptable other components (for example, carriers, excipients, disintegrating agents, buffers, emulsifying agents, suspending agents, soothing agents, stabilizers, preservatives, antiseptics, and a normal saline solution). Examples of the excipient include lactose, starch, sorbitol, D-mannitol, and white sugar. Examples of the disintegrating agent include starch, carboxymethyl cellulose, and calcium carbonate. Examples of the buffer include phosphates, citrates, and acetates. Examples of the emulsifying agent include gum arabic, sodium alginate, and gum tragacanth. Examples of the suspending agent include glycerol monostearate, aluminum monostearate, methyl cellulose, carboxymethyl cellulose, hydroxymethyl cellulose, and sodium lauryl sulfate. Examples of the soothing agent include benzyl alcohol, chlorobutanol, and sorbitol. Examples of the stabilizer include propylene glycol and ascorbic acid. Examples of the preservative include phenol, benzalkonium chloride, benzyl alcohol, chlorobutanol, and methylparaben. Examples of the antiseptic include benzalkonium chloride, paraoxybenzoic acid, and chlorobutanol.

The dosage form of the formulation is not particularly limited, either. The pharmaceutical composition or quasi drug composition of the present invention may be in the form of, for example, tablet, powder, fine grain, granule, capsule, syrup, injection, external preparation, or suppository.

The pharmaceutical composition of the present invention contains active components in amounts necessary for achieving expected therapeutic effect and preventive effect (more specifically, therapeutically effective dose). The quasi drug composition of the present invention also contains active components in amounts necessary for achieving expected therapeutic effect and preventive effect. The amount of the active components contained in the pharmaceutical composition or quasi drug composition of the present invention commonly depends on the dosage form and shape. In order to achieve the desired dose, the amount of the active components is set at, for example, in the range of about 0.1% to 95% by weight.

The pharmaceutical composition and quasi drug composition of the present invention are administered to the subject orally or parenterally (for example, intravenous, intraarterial, hypodermic, muscle, or intraperitoneal injection, transdermal, nasotracheal, or transmucosal administration, or application), depending on the dosage form or shape. The "subject" is not particularly limited, and examples thereof include human and mammals other than human (for example, pet animals, livestock, and experimental animals, and specific examples include mice, rats, guinea pigs, hamsters, monkeys, bovines, pigs, goats, sheep, dogs, cats, chickens, and partridges). In a preferred embodiment, the subject is human.

The dosage and usage of the pharmaceutical composition and quasi drug composition of the present invention are established so as to achieve the expected effect. The effective dose is commonly established in consideration of the symptom, age, sex, and body weight of the subject. Those skilled in the art can establish the appropriate dose in consideration of these factors. The administration schedule may be, for example, once to several times a day, once in two days, or once in three days. The administration schedule may be arranged in consideration of the symptom of the subject and effect duration time of the active components.

As described above, one aspect of the present invention is a food composition containing the solubilized eggshell membranes obtained by the eggshell membrane solubilization method of the present invention. Examples of the "food composition" of the present invention include general food (grains, vegetable, meat, various processed foods, confectionery, milk, refreshing drinks, and alcohols), dietary supplements (supplements and nutritional drinks for the purpose of prevention of oxidation, inhibition of growth of bacteria, prevention of inflammation, wound healing, blood pressure lowering, and anti-aging), and food additives. The dietary supplement or food additive may be provided in the form of powder, granule, tablet, paste, or liquid. When the solubilized eggshell membranes obtained by the eggshell membrane solubilization method of the present invention are provided in the form of a food composition, the solubilized eggshell membranes can be routinely or continuously taken.

The loading of the solubilized eggshell membranes may be freely established according to the intended use. For example, when the food composition of the present invention is expected to contribute to the maintenance or enhancement of health, or the treatment or prevention of specific diseases or clinical conditions, the food composition preferably contain the solubilized eggshell membranes in an amount enough for these effects. The loading may be established in consideration of the food type, food consumer (for example, sex, age, and body weight), and the effects expected from the food.

As described above, one aspect of the present invention is a cosmetic composition containing the solubilized eggshell membranes obtained by the eggshell membrane solubilization method of the present invention. The cosmetic composition of the present invention is obtained by mixing the solubilized eggshell membranes, general components and base materials of cosmetics (for example, various fats and oils, mineral oil, vaseline, squalane, lanoline, beeswax, denatured alcohol, palmitic acid dextrin, glycerin, glycerin fatty acid ester, ethylene glycol, paraben, camphor, menthol, various vitamin, zinc oxide, titanium oxide, benzoic acid, edetic acid, camomile oil, carrageenan, chitin powder, chitosan, perfume, or colorant). Examples of the form of the cosmetic composition include face or body milky lotion, skin lotion, cream, lotion, essence, oil, facial mask, sheet, and cleanser. The loading of the solubilized eggshell membranes in the cosmetic composition is not particularly limited. For example, the loading of the solubilized eggshell membranes is from 0.1% by weight to 60% by weight. Examples of the application or effect of the cosmetic composition of the present invention include moisture retention, infiltration, prevention of skin roughening, skin beautification, and prevention of wrinkling, sagging, or aging.

The solubilized eggshell membranes of the present invention are also useful in, for example, the recovery of metal ions, humectants, absorbents, antibacterial substances, and hair growth tonics.

4. Method for Extracting Useful Components from Eggshell Membranes

The present invention also provides a method for extracting useful components from eggshell membranes using the eggshell membrane solubilization method of the present invention. The method of the present invention for extracting useful components from eggshell membranes includes the following steps (i) and (ii):

(i) a solubilization step according to the eggshell membrane solubilization method of the present invention; and (ii) a step of purifying the solubilized eggshell membranes obtained by the solubilization step.

In the step (ii), purification is carried out through the appropriate combination of filtration, centrifugation, demineralization, salting out such as ammonium sulfate precipitation, dialysis, and various kinds of chromatography (for example, ion exchange chromatography, hydrophobic chromatography, and affinity chromatography). Examples of the useful component to be purified include enzymes such as lysozyme, lysyl oxidase, and β-N-acetylglucosaminidase, and acid mucopolysaccharides such as hyaluronic acid, chondroitin sulfate, and dermatan sulfate. The purification may be carried out in steps, thereby obtaining two or more useful components.

The useful components of eggshell membranes obtained by the method of the present invention may be used as the components included in or added to, for example, medicines, foods, or cosmetics, in the same manner as solubilized eggshell membranes.

EXAMPLES

1. Study of Eggshell Membrane Solubilization by Protease

Chicken eggs were broken and liquid eggs were taken out, and then the egg shells with eggshell membranes were immersed in a 4% by weight acetic acid aqueous solution for about 5 to 10 minutes, and the eggshell membranes were removed and collected by hand. The removed eggshell membranes were washed with water, and thoroughly dried before use.

Using the eggshell membranes as substrates, solubilization of the eggshell membranes was studied using existing enzyme preparations. Using 15 commercially available enzyme preparations (NEWLASE F3G, PROTEASE M, PROTEASE N, PROTEASE P3G, PROTEASE S, BROMELAIN F, PROLEATHER FG-F, peptidase R, UMAMIZYME G, THERMOASE Y100, PROTEAX, PROTEASE A, PAPAIN W40, PANCREATIN 8AP, and BIOSORK), reaction was carried out under various pH conditions (pH 4.0 to 13.0). The buffer solutions in the respective pH ranges are as follows. The conditions at pH 4.0 and 5.0 used a 100 mM NaOAc buffer, pH 6.0 used a 100 mM MES-NaOH buffer, pH 7.0 used a 100 mM HEPES-NaOH buffer, pH 8.0 used a 100 mM Tris-HCl buffer, pH 9.0 to 12.0 used a 100 mM Glycine-NaOH buffer, and pH 13.0 used a 100 mM KCl—NaOH buffer. The enzyme concentration was 0.1% (w/v), the eggshell membrane concentration was 1.0% (w/v), the reaction temperature was 60° C., and the incubation time was 72 hours. FIG. 1 shows the result using BIOSORK as the test enzyme preparation. The result indicates that solubilization (decomposition) of eggshell membranes were not detected by visual observation, even after the reaction for 72 hours. Solubilization was not detected by visual observation when other 14 enzyme preparations were used.

2. Study of Eggshell Membrane Solubilization by Coexistence of Protease and Reducing Agent Solubilization of eggshell membranes did not occur with the enzyme preparation alone, so that the effect of the combination with a reducing agent was examined. In the present test, the test enzyme preparations were BIOSORK and PROLEATHER FG-F. Using 100 mM Glycine-NaOH at pH 9.0 as the buffer solution, solubilization was attempted with or without addition of 10 mM DTT. Incubation was carried out under conditions that the enzyme concentration was 0.1% (w/v), the eggshell membrane concentration was 1.0% (w/v), and the reaction temperature was 60° C. FIG. 2 shows the result of the case using BIOSORK as the test enzyme preparation. As shown in FIG. 2, eggshell membranes were not solubilized by DTT or enzyme preparation alone, but were solubilized in as short as 1.5 hours in the coexistence of DTT and enzyme preparation. The same result was obtained when PROLEATHER FG-F was used, but the time required for complete solubilization was longer than the case using BIOSORK (about 2 hours). The reason for this is likely that the reducing agent cleaved the disulfide bonds contained in the protein composing the eggshell membranes, and thus facilitating the solubilization. In addition, on the basis of the fact that the solubilization was inhibited by PMSF which is a serine protease inhibitor, the solubilization of eggshell membranes in the present test is likely due to a protease.

3. Study of Eggshell Membrane Solubilization by the Coexistence of Protease and Reducing Agent (Food Additive)

In consideration of safety and cost, reducing agents which allows solubilization of eggshell membranes were selected from food additives. Firstly, using BIOSORK as the test enzyme preparation, solubilization was attempted using any of the ten reducing agents (sodium sulfite, sodium hydrogensulfite, L-ascorbic acid, L-cysteine hydrochloride, sodium nitrite, sodium nitrate, L-cysteine, glutathione, DTT, sodium borohydride, HITHION EXTRACT YH-8, HITHION EXTRACT YH-15, and HITHION EXTRACT YH-D12). The tested concentrations of sodium sulfite, sodium hydrogensulfite, L-ascorbic acid, sodium nitrite, sodium nitrate, DTT, and sodium borohydride were 1, 10, and 100 mM. The tested concentrations of L-cysteine hydrochloride, L-cysteine, and glutathione were 1, 10, 20, and 50 mM. The tested concentrations of HITHION EXTRACT YH-8, HITHION EXTRACT YH-15, and HITHION EXTRACT YH-D12 were 1, 5, and 10% (w/v). The pH conditions of the buffer solution were from 4.0 to 13.0, and the same buffer solution as descried above were used. The enzyme concentration was 0.1% or 0.5% (w/v), the eggshell membrane concentration was 1.0% (w/v), the reaction temperature was 60° C., and the incubation was carried out for 6 or 12 hours. In the comparison of the decomposing ability at different pHs in the presence of sodium sulfite, the concentration of sodium sulfite was 100 mM, and the pH of the buffer solutions (100 mM) was from 4.0 to 13.0. In the tests using BIOSORK and PROLEATHER FG-F, the NaOAc buffer, MES-NaOH buffer, HEPES-NaOH buffer, Tris-HCl buffer, Glycine-NaOH buffer, and KCl—NaOH buffers were used for the pH range from 4.0 to 5.5, 5.5 to 6.5, 6.5 to 7.5, 7.5 to 9.0, 9.0 to 12.5, and 12.5 to 13.0, respectively. In the tests using the other 13 enzyme preparations, the NaOAc buffer (pH 4.0 and 5.0), MES-NaOH buffer (pH 6.0), HEPES-NaOH buffer (pH 7.0), Tris-HCl buffer (pH 8.0), and Glycine-NaOH buffer (pH 9.0) were used. Incubation was carried out under conditions that the enzyme concentration was 0.1% (w/v), the eggshell membrane concentration was 1.0% (w/v), and the reaction temperature was 60° C., and the time required for complete solubilization was measured. In the confirmation of the decomposition pattern, using BIOSORK and PROLEATHER FG-F as the test enzyme preparations, PMSF was added to the solution after reaction at different pH conditions to give the final concentration of 1 mM to stop the reaction, and the samples thus obtained were subjected to SDS-PAGE. FIG. 3 shows the type of the tested reducing agents and the presence or absence of the occurrence of solubilization (decomposition) of eggshell membranes. Of the food additives, sulfites and hydrogensulfites exhibited marked effects at the concentration of 100 mM. When sodium sulfite was used, eggshell membranes were efficiently solubilized at pH 6.0 to 8.0. When L-cysteine was used, eggshell membranes were partially solubilized.

Subsequently, the decomposing abilities at different pHs in the presence of sodium sulfite were compared. FIG. 4 shows the result obtained using BIOSORK, wherein the abscissa indicates the pH at the time of reaction, and the ordinate indicates the time required for the complete solubilization of eggshell membranes. The pH at the time of reaction indicated on the abscissa is not the pH at the time of adjustment, but the pH during the actual reaction. The correspondence table of the pHs at the time of adjustment and reaction is shown in Table 1.

TABLE 1

|  | pH at the time of adjustment | pH in the reaction solution (60° C.) |
| --- | --- | --- |
| NaOAC | 4 | 4.75 |
|  | 4.5 | 6.08 |
|  | 5 | 7.17 |
|  | 5.5 | 7.77 |
| MES-NaOH | 5.5 | 7.34 |
|  | 6 | 7.33 |
|  | 6.5 | 7.65 |
| HEPES-NaOH | 6.5 | 7.43 |
|  | 7 | 7.55 |
|  | 7.5 | 7.77 |
| Tris-HCl | 7.5 | 7.88 |
|  | 8 | 8.13 |
|  | 8.5 | 8.53 |
|  | 9 | 8.92 |
| Glycine-NaOH | 9 | 8.73 |
|  | 9.5 | 9.2 |
|  | 10 | 9.64 |
|  | 10.5 | 10.15 |
|  | 11 | 10.55 |
|  | 11.5 | 10.72 |
|  | 12 | 10.83 |
|  | 12.5 | 10.94 |
| KCl—NaOH | 12.5 | 10.45 |
|  | 13 | 11.15 |

As shown in FIG. 4, efficient solubilization occurred in the presence of sodium sulfite at pH 6.0 to 8.0. BIOSORK and other nine enzyme preparations including PROLEATHER FG-F caused efficient solubilization of eggshell membranes in the vicinity of pH 7.0. Table 2 shows the enzyme preparations arranged in order of rapidity of solubilization of eggshell membranes under their optimum pH conditions.

TABLE 2

| | Trade name | Time required for solubilization* |
|---|---|---|
| 1 | BIOSORK | 1 hour 15 minutes |
| 2 | PROLEATHER FG-F | 2 hours |
| 3 | PAPAIN W40 | 2 hours |
| 4 | PROTEASE N | 3 hours |
| 5 | BROMELAIN F | 4 hours 45 minutes |
| 6 | UMAMIZYME G | 5 hours |
| 7 | THERMOASE Y100 | 5 hours 30 minutes |
| 8 | PROTEAX | 7 hours 15 minutes |
| 9 | PROTEASE S | 7 hours 15 minutes |
| 10 | PANCREATIN 8AP | >12 hours |

*Time required under optimum conditions

It is known that the reduction action of sodium sulfite is highest in the vicinity of pH 7.0, and the present result accords with this finding. On the other hand, the optimum pH of BIOSORK is from 10.5 to 11.5, but solubilization did not occur under these pH conditions. These facts suggest that solubilization of eggshell membranes markedly depends on the effect of the reducing agent.

PMSF was added to the samples which caused solubilization of eggshell membranes thereby deactivating BIOSORK or PROLEATHER FG-F, and the samples were subjected to SDS-PAGE (FIG. 5). The molecular weights of the solubilized product were from 3.5 to 25 kDa, and many of them were in the vicinity of 6 kDa. In addition, a thick band was observed in the vicinity of 14 kDa.

4. Concentration Dependence of Sodium Sulfite in Eggshell Membrane Solubilization The optimum concentration of sodium sulfite for the solubilization of eggshell membranes was searched. In the present test, BIOSORK and PROLEATHER FG-F were used as the test enzyme preparations. 50 mM Tris-HCl at pH 7.0 was used as the buffer solution, and solubilization was attempted with or without addition of 10 to 1000 mM sodium sulfite. Incubation was carried out under conditions that the enzyme concentration was 0.1% (w/v), the eggshell membrane concentration was 1.0% (w/v), and the reaction temperature was 60° C., and the time required for complete solubilization was measured. As shown in FIG. 6, the optimum concentration of sodium sulfite was 200 mM for BIOSORK and PROLEATHER FG-F. On the other hand, it was confirmed that solubilization occurred in a wide concentration range from 10 to 1000 mM. FIGS. 7 and 8 show the results of solubilization of eggshell membranes using BIOSORK and PROLEATHER FG-F, respectively.

5. Enzyme Concentration Dependence of Eggshell Membrane Solubilization

The optimum enzyme concentration for the solubilization of eggshell membranes was searched. In the present test, the test enzyme preparation was BIOSORK. The buffer solution was 50 mM Tris-HCl at pH 7.0, and solubilization was attempted with the addition of 200 mM sodium sulfite. Incubation was carried out under conditions that the enzyme concentration was 0.01, 0.1, or 1.0% (w/v), the eggshell membrane concentration was 10% (w/v), and the reaction temperature was 60° C., and the time required for complete solubilization was measured. From this test, stirring was carried out during incubation. As shown in Table 3, when BIOSORK was used, the eggshell membranes were completely solubilized in 45 minutes at the concentration of 1.0%, and 60 minutes at the concentration of 0.1%. On the other hand, no solubilization occurred at the concentration of 0.01%. In the present test, the eggshell membrane concentration was increased to 10% (w/v), but the solubilization time was shorter than the case wherein the eggshell membrane concentration was 1% (w/v). This is likely due to the influence of stirring. Regarding the enzyme concentration, 1.0% and 0.1% are likely not so different. In consideration of the cost, the use at 0.1% is likely more efficient.

TABLE 3

| Enzyme concentration | Time |
|---|---|
| 0.01% | 24 hours or more |
| 0.1% | 60 minutes |
| 1.0% | 45 minutes |

6. Solubilization Time at Different Eggshell Membrane Concentrations

The eggshell membrane concentration was changed, and the highest concentration which can be solubilized was studied. In the present test, the test enzyme preparation was BIOSORK. Using 50 mM Tris-HCl at pH 7.0 was used as the buffer solution, and solubilization was attempted with the addition of 200 mM sodium sulfite. Incubation was carried out under conditions that the enzyme concentration was 0.1 (w/v), the eggshell membrane concentration was from 10 to 50% (w/v), and the reaction temperature was 60° C., and the time required for complete solubilization was measured. Also in the present test, stirring was carried out during incubation. As shown in FIG. 9 left, the eggshell membranes were completely solubilized even at the concentrations of 10 to 50%. FIG. 9 right shows the graph of the solubilization time at different eggshell membrane concentrations. The abscissa indicates the eggshell membrane concentration, and the ordinate indicates the time required for solubilization, and the time required for complete solubilization at different eggshell membrane concentrations is plotted. The plots are on a straight line at the eggshell membrane concentrations of 10 to 40%, indicating that decomposition reaction progressed at the same efficiency.

7. Search of Protease Allowing Solubilization of Eggshell Membranes in the Presence of Reducing Agent Of the 15 commercially available enzyme preparations, ten enzyme preparations caused solubilization of eggshell membranes in the presence of a reducing agent, particularly sodium sulfite. These ten enzyme preparations included neutral and alkaline proteases. In the present experiment, with the intention of verifying the ability of acidic proteases to decompose eggshell membranes, the presence or absence of decomposing ability was examined using a plurality of acidic proteases. In addition, the experiments using new neutral and alkaline proteases were also carried out in parallel.

The following enzyme preparations were studied.

(1) Acidic protease: SUMIZYME AP (*Aspergillus niger*-derived acidic protease, Shinnihon Chemicals Corporation), PEPSIN (Sigma)

(2) Neutral protease: SUMIZYME FP (*Aspergillus oryzae*-derived neutral protease, Shinnihon Chemicals Corporation), SUMIZYME LP500 (*Aspergillus oryzae*-derived neutral protease, Shinnihon Chemicals Corporation), SUMIZYME LPL (*Aspergillus oryzae*-derived neutral protease, Shinnihon Chemicals Corporation), DESKIN C (origin is unknown, neutral protease, Daiwa Fine Chemicals Co., Ltd.), PROTIN NY10 (*Bucillus subtilis*-derived neutral protease, Daiwa Fine Chemicals Co., Ltd.), PROTIN PC10 (*Bucillus subtilis*-derived neutral protease, Daiwa Fine Chemicals Co., Ltd.), TRYPSIN (Roche)

(3) Alkaline protease: SUMIZYME MP (*Aspergillus* sp.-derived alkaline protease, Shinnihon Chemicals Corporation), PROTIN AY (*Bucillus licheniformis*-derived alkaline protease, Daiwa Fine Chemicals Co., Ltd.), PROTEINASE K (Roche)

The reducing agent was sodium sulfite (Kanto Chemical Co., Inc.), and added in an amount to give the final concentration of 100 mM. The buffer solutions were a 100 mM NaOAc buffer for acidic pH conditions (pH 4.5 or pH 4.7), a 100 mM Tris-HCl buffer for neutral pH conditions (pH 7.0 or pH 7.5), and a 100 mM GLycine-NaOH buffer for alkaline pH conditions (pH 9.0 or pH 8.7). The enzyme was added to give the final concentration of 0.1% (w/v). Incubation was carried out at 50° C. for 24 hours, and the presence or absence of occurrence of eggshell membrane solubilization was studied.

PEPSIN (FIG. 10) shows marked solubilization in the presence of the reducing agent under acidic pH conditions. PEPSIN did not achieve complete solubilization, but the increase of the enzyme concentration will allow complete solubilization. Regarding neutral proteases, SUMIZYME LP500 (FIG. 11), DESKIN C (FIG. 12), PROTIN NY10 (FIG. 13), PROTIN PC10 (FIG. 14), and TRYPSIN (FIG. 15) solubilized eggshell membranes in the presence of the reducing agent. Regarding alkaline proteases, SUMIZYME MP (FIG. 16), PROTIN AY (FIG. 17), and PPOTEINASE K (FIG. 18) caused solubilization.

The above-described results indicate that the acidic protease solubilizes eggshell membranes in the presence of a reducing agent. Accordingly, solubilization of eggshell membranes can be achieved by any of acidic, neutral, or alkaline protease in the presence of a reducing agent. In addition, eight enzyme preparations were newly found as neutral and alkaline proteases which solubilize eggshell membranes in the presence of a reducing agent.

8. Search of New Candidates of Reducing Agent

As described above, it was found that the addition of a reducing agent is effective for the efficient solubilization of eggshell membranes with a protease. Up to now, as the reducing agents allowing solubilization of eggshell membranes, sodium sulfite (Kanto Chemical Co., Inc.), sodium hydrogensulfite (Wako Pure Chemical Industries, Ltd.), L-cysteine (Sigma Aldrich), and DTT (Wako Pure Chemical Industries, Ltd.) were found. As described below, several reducing agents were newly subjected to solubilization test.

In the present test, BIOSORK and PROLEATHER FG-F were used as test enzyme preparations. The enzyme concentration was 0.1% (w/v). The buffer solutions were 100 mM Tris-HCl at pH 7.0 and 100 mM Glycine-NaOH at pH 9.0. As the reducing agents, five products, or (1) N-acetyl-L-cysteine (Wako Pure Chemical Industries, Ltd.), (2) 2-mercaptoethanol (Wako Pure Chemical Industries, Ltd.), (3) thioglycolic acid (Wako Pure Chemical Industries, Ltd.), (4) sodium thiosulfate (Wako Pure Chemical Industries, Ltd.), and (5) thiourea (Wako Pure Chemical Industries, Ltd.) were tested. These reducing agents were added to give the final concentrations of 1, 10, and 100 mM, and incubated at 50° C. for 24 hours, thereby studying the presence or absence of the occurrence of solubilization of eggshell membranes.

Of the five reducing agents tested, BIOSORK and PROLEATHER FG-F caused solubilization of eggshell membranes when N-acetyl-L-cysteine (FIG. 19) or 2-mercaptoethanol (FIG. 20) was added. N-acetyl-L-cysteine caused partial solubilization, but likely achieves complete solubilization when the enzyme concentration is increased. When the reducing agent was 2-mercaptoethanol, complete solubilization was achieved. N-acetyl-L-cysteine and 2-mercaptoethanol are known to cleave disulfide bonds. This fact suggests that cleavage of disulfide bonds is important and effective for the solubilization of eggshell membranes.

9. Identification of Acid Mucopolysaccharide in Solubilized Eggshell Membranes

It is known that eggshell membranes contain a collagen-like protein, as well as, sulfated glycosaminoglycans (GAG) such as dermatan sulfate and chondroitin sulfate, and hyaluronic acid. These acid mucopolysaccharides are used for the treatment of arthropathy and cosmetics having water retentivity. Accordingly, if the presence of these polysaccharides is found in the solubilized eggshell membranes obtained by the present method, the utility value of the solubilized eggshell membranes will be increased. Therefore, in the present experiment, the identification of sulfated GAGs and hyaluronic acid was attempted using the solubilized eggshell membranes obtained herein.

Firstly, solubilized eggshell membranes were prepared. An enzyme preparation was added to the reaction solution (50 mM Tris-HCl pH 7.0, 100 mM sodium sulfite) containing 10% (w/v) eggshell membranes, thereby solubilizing the eggshell membranes. The enzyme preparations were PROTEINASE K (Roche), BIOSORK, PROLEATHER FG-F, and PAPAIN W40. PROTEINASE K was added in an amount to give the final concentration of 0.01% (w/v), and the other enzyme preparations were added to give the final concentration of 0.1% (w/v). After the addition of any of these enzyme preparations, incubation was carried out at 50° C. for 12 hours under stirring, thereby completely solubilizing the eggshell membranes. As the control, a sample free from eggshell membrane and containing an enzyme preparation and a reducing agent was prepared.

Using these samples, identification of sulfated GAGs was attempted. Examples of the common procedure for detecting sulfated GAGs include a colorimetric method (Farndale, et al. (1986) Biochim. Biophys. Acta. 883, 173-177.) and an HPLC method (Japanese Unexamined Patent Application Publication No. 4-135496). From the viewpoints of general-purpose properties, easiness, operational results, and the like, the colorimetric method with 1,9-dimethylmethylene blue (DMMB) was used. The absorption wavelength of 1,9-DMMB is 595 nm when it is not reacted with a sulfated GAG, and changes to 525 nm upon reaction with a sulfated GAG. Accordingly, the higher the value measured at 525 nm, the higher the content of sulfated GAGs. A calibration curve was prepared using chondroitin sulfate at known concentrations (2.5, 5, 7.5, 10, 15, and 20 μg/mL) as the standard sample, and the values of the samples at 525 nm were measured, thereby calculating the content of sulfated GAGs. The measurement was carried out as follows: 1 mL of 1,9-DMMB solution (16 mg of 1,9-DMMB (Biochemica), 3.0 g of glycine, 2.37 g of NaCl, 95 mL of 0.1 N HCl, and 904 mL of $H_2O$) and 40 μL of the sample were mixed, stirred, and then the value at 525 nm was measured by a microplate reader.

The identification of hyaluronic acid in the samples was carried out using a commercially available hyaluronic acid measurement kit (Seikagaku Corporation). This kit is based on the inhibition process using a hyaluronic acid-bonding protein (HABP), and allows specific detection of hyaluronic acid.

The contents of sulfated GAGs in the solubilized eggshell membranes treated with the enzyme preparations are shown in FIG. 21. The content is the value for the unit mass of eggshell membranes, and the mass of the eggshell membranes was measured before the enzyme preparation treatment. The value of the control was subtracted from the contents of the samples. As shown in FIG. 21, it was found that the solubilized eggshell membranes obtained by the present experiment contained sulfated GAGs (the content is 0.53 to 5.4% (w/w) for unit mass of the eggshell membranes).

The content of hyaluronic acid in the solubilized eggshell membranes is shown in FIG. 22. The content is the value for the unit mass of eggshell membranes, and the value of the control was subtracted from the content. As indicated by the result, it was found that the solubilized eggshell membranes contained hyaluronic acid (the content is 0.026 to 0.11% (w/w) for the unit mass of the eggshell membranes).

As described above, it was found that the solubilized eggshell membranes obtained by the present eggshell membrane solubilization method (combination of a protease and a reducing agent) contains acid mucopolysaccharides such as sulfated GAGs and hyaluronic acid. As described above, the utility value of acid mucopolysaccharides is high. Accordingly, the utility value of the solubilized product is regarded very high.

10. Identification of Lysyl Oxidase Activity in Solubilized Eggshell Membranes

It is known that lysyl oxidase (EC 1.4.3.13) is present in eggshell membranes. The enzyme causes oxidative deamination of the ε-amino group of the lysine residue in protein to form aldehyde (allicin residue), and participates to the crosslinking reaction of proteins such as collagen and elastin. The crosslinking reaction is a specific process indispensable for the functional expression such as skin elasticity or extensibility, and construction of tissues. Accordingly, the utility value of the solubilized eggshell membranes obtained by the present method will be increased if lysyl oxidase activity is identified therein. Therefore, in the present experiment, the detection of lysyl oxidase activity was attempted using solubilized eggshell membranes.

Firstly, solubilized eggshell membranes were prepared using the combination of a reducing agent and a protease. An enzyme preparation was added to a reaction solution (100 mM PBS buffer at pH 7.4, 100 mM sodium sulfite) containing 10% (w/v) eggshell membranes, thereby solubilizing the eggshell membranes. The enzyme preparation was PROTEINASE K (Roche), BIOSORK, PROLEATHER FG-F, or PAPAIN W40, and the PROTEINASE K was added in an amount to give the final concentration of 0.01% (w/v), and the other enzyme preparations were added in amounts to give the final concentration of 0.1% (w/v). After the addition of the enzyme preparation, incubation was carried out at 50° C. for 12 hours under stirring, thereby completely solubilizing the eggshell membrane. As the control, a sample free from eggshell membrane and containing an enzyme preparation and a reducing agent was prepared. Subsequently, n-butylamine was added to the solution of the solubilized product to give the final concentration of 10 mM, and incubated at 37° C. for 60 minutes. At that time, if lysyl oxidase is present in the solubilized product, n-butylamine is oxidized to form n-butylaldehyde. The n-butylaldehyde was detected using an Nash reagent (15% (w/v) ammonium acetate, 0.5% (w/w) acetic acid, 20% (w/w) acetylacetone, Nash, et al. (1953) BioChem. J. 55, 416.). Specifically, the Nash reagent and the sample were mixed in equal amounts, incubated at 50° C. for 30 minutes; n-butylaldehyde in the reaction liquid reacts with the Nash reagent to form a yellow color substance which can be detected at 388 nm. The higher the value at 388 nm, the higher the lysyl oxidase activity. Using the sample after incubation, the value at 388 nm was measured with a microplate reader.

Secondly, the eggshell membrane was treated with a reducing agent, the reducing agent was removed, and then the solubilized eggshell membranes treated with a protease were prepared. Firstly, about 500 mg of eggshell membranes were added to 5 mL of reducing agent solution (100 mM PBS buffer at pH 7.4, 100 mM sodium sulfite), and incubated at 37° C. for 1 hour. Thereafter, the eggshell membranes were taken out, washed with 50 mL portion of distilled water five times, and finally washed with 500 mL of distilled water, thereby removing sodium sulfite. The eggshell membranes after washing were lightly drained, 5 mL of a solution containing 0.1% (w/v) BIOSORK (100 mM PBS buffer pH 7.4) was added thereto, and incubated at 37° C. 200 μL of samples were collected at different times (0, 1, 2, 3, 4, and 6 hours), and the lysyl oxidase activity of these samples was measured. 20 μL of 100 mM n-butylamine was added to these samples (final concentration 10 mM), and incubated at 37° C. for 45 minutes. Thereafter, 220 μL of Nash reagent was added, incubated at 50° C. for 30 minutes, and then the value at 388 nm was measured using a microplate reader.

No lysyl oxidase activity was detected in the samples of the solubilized eggshell membranes prepared using the combination of a reducing agent and a protease. Lysyl oxidase is an oxidative enzyme and may be deactivated by the reducing agent. In particular, the lysyl oxidase liberated in the solution by the decomposition of the protease may be markedly influenced by the reducing agent. On the other hand, lysyl oxidase activity was detected in the solubilized eggshell membranes which had been prepared by treating eggshell membranes with a reducing agent, removing the reducing agent, and then treating the membranes with a protease (FIG. 23). In addition, the activity increased with the lapse of time of the protease treatment. No lysyl oxidase activity was detected in the control, indicating that the activity is attributable to the lysyl oxidase derived from the eggshell membranes. Lysyl oxidase activity was detected in the eggshell membranes which had been subjected to enzyme treatment without reducing agent treatment, but the activity was about one half to one third that of the eggshell membranes treated with a reducing agent. Accordingly, the treatment of eggshell membranes with a reducing agent is regarded as effective for the efficient recovery of lysyl oxidase.

As described above, it has been found that lysyl oxidase is efficiently recovered through the three steps: (1) treatment of eggshell membranes with a reducing agent, (2) removal of the reducing agent, and (3) protease treatment.

11. Identification of Bacteriolysis (Antibacterial) Activity in Solubilized Eggshell Membranes Eggshell membranes contain the enzymes having bacteriolysis (antibacterial) activity, such as lysozyme (EC 3.2.1.17) and β-N-acetylglucosaminidase (EC 3.2.1.96). If these enzymes are present in the solubilized eggshell membranes obtained by the present method, the applications of the solubilized product will be increased. In the present experiment, the presence or absence of bacteriolysis activity was examined using solubilized eggshell membranes.

Firstly, solubilized eggshell membranes were prepared. Eggshell membranes were solubilized by adding an enzyme preparation to a reaction solution (100 mM PBS buffer pH 7.0, 100 mM sodium sulfite) containing 10% (w/v) eggshell membranes. The test enzyme preparation was any of BIOSORK, PROLEATHER FG-F, or PAPAIN W40, and added to give the final concentration of 0.5% (w/v). After the addition of the enzyme preparation, incubation was carried out at 37° C. for 12 hours under stirring, thereby completely solubilizing the eggshell membranes. As the control, a sample free from eggshell membrane and containing an enzyme preparation and a reducing agent was prepared.

In the measurement of bacteriolysis activity, *Micrococcus Luteus* (Wako Pure Chemical Industries, Ltd.) is commonly used as the test bacterium to be the substrate. The bacterial cell powder was suspended in 100 mM PBS buffer at pH 7.0 to give the final concentration of 0.32 mg/mL 10 μL of any of the solubilized eggshell membrane samples was added to a microplate (Nunc), and then 240 μL of the bacterial cell suspension was added to the sample. The value at 450 nm was measured immediately after the addition, incubation at 37° C. was started, and the value at 450 nm was measured at intervals of 10 minutes. The clarity of the suspension increases and thus the value at 450 nm decreases with the progress of bacteriolysis. The faster the decrease of the value at 450 nm, the higher the bacteriolysis activity.

As shown in FIG. 24, bacteriolysis activity was detected in all the solubilized eggshell membranes treated with the enzyme preparations. Although the degrees are different, the bacteriolysis activity is evident. No bacteriolysis activity was detected in the control, indicating that the activity is derived from the eggshell membranes.

The above results suggest that the solubilized eggshell membranes obtained by the present method contains an enzyme having bacteriolysis activity, and that the enzyme is lysozyme and/or β-N-acetylglucosaminidase.

12. Antioxidative Ability of Solubilized Eggshell Membranes

It is known that the major cause of cancer, life-style diseases, and body aging is oxidative stress due to active oxygen, free radical, or lipid peroxide. Vitamin C, vitamin E, β-carotene, and the like are used as antioxidative substances preventing oxidative stress. In addition, antioxidative peptides derived from proteins are receiving attention from the viewpoint of safety. In particular, peptides having cysteine residues, such as glutathione exhibit high antioxidative ability. About 10% of amino acids composing an eggshell membrane is cysteine (cystine), so that the solubilized eggshell membrane is expected to have high antioxidative ability. In the present experiment, the solubilized eggshell membranes obtained by the present method were measured for their antioxidative activity, thereby examining their possibility as a material having antioxidative ability.

Firstly, solubilized eggshell membranes were prepared. Eggshell membranes were solubilized by adding an enzyme preparation to a reaction solution (100 mM PBS buffer pH 7.0, 100 mM sodium sulfite) containing 10% (w/v) eggshell membranes. The test enzyme preparation was any of BIOSORK, PROLEATHER FG-F, or PAPAIN W40, and added to give the final concentration of 0.5% (w/v). After the addition of the enzyme preparation, incubation was carried out at 37° C. for 12 hours under stirring, thereby completely solubilizing the eggshell membranes. As the control, a sample free from eggshell membrane and containing an enzyme preparation and a reducing agent was prepared.

The antioxidative ability was measured by the modification of the method of Ikuo Suda using DPPH (1,1-Diphenyl-2-picrylhydrazol) measuring the free radical scavenging ability ("Food Function Manuals", 16, Agriculture, Forestry and Fisheries Research Council, National Agriculture and Food Research Organization, 1999). More specifically, 5 μL of any of the samples was added to a microplate, additionally 245 μL of 0.5 mM DPPH-EtOH solution was added, and then the absorbance at 520 nm was measured after the lapse of two minutes. 1.0 mM Trolox (antioxidative substance) was used as the standard reagent, thereby expressing the antioxidative activity of the samples in terms of the Trolox equivalent (μmol Trolox equivalent/100 g). The mass by 100 g is the mass of eggshell membranes, and the value measured before the solubilization reaction.

Subsequently, the antioxidative ability was measured making use of copper reduction using an antioxidative ability measurement kit "PAO" (Japan Institute for the Control of Aging). The copper reducing ability test is the test of antioxidation ability using the reduction reaction of copper ions ($Cu^{2+} \rightarrow Cu^{+}$).

The control value was subtracted from the value of the antioxidative activity of the solubilized eggshell membranes determined by the above-described two methods.

As shown in FIG. 25, the solubilized eggshell membranes treated with the enzyme preparations were found to have free radical scavenging activity. The activity values were 678.3, 521.7, and 415.2 μmmol Trolox equivalent/100 g for the eggshell membranes solubilized with BIOSORK, PROLEATHER FG-F, and PAPAIN W40, respectively. In addition, as shown in FIG. 26, copper-reducing activity was also found. The activity values of the samples were relatively high; 3617.1, 2090.8, and 2816.8 μmol/L for the eggshell membranes solubilized with BIOSORK, PROLEATHER FG-F, and PAPAIN W40, respectively.

As described above, the solubilized eggshell membranes obtained by the present method were found to have relatively high antioxidative ability. Accordingly, the solubilized product is regarded as a useful functional material having antioxidative ability.

13. ACE-Inhibiting Activity of Solubilized Eggshell Membranes

Angiotensin converting enzyme (ACE) has a very important role in the blood pressure regulation mechanism of human. ACE is an enzyme closely related with the blood pressure elevation, and forms angiotensin II having vasopressor action from angiotensin I in the renin-angiotensin system, which is one of blood pressure regulation mechanisms. In recent years, food components having ACE-inhibiting effect are receiving attention, and many functional foods (foods for specified health use) with the intention of hypertension prevention are on the market. Accordingly, in the present experiment, the solubilized eggshell membranes obtained by the present method were measured for the ACE-inhibiting activity to study whether the material has antihypertensive action.

Firstly, solubilized eggshell membranes were prepared. Eggshell membranes were solubilized by adding an enzyme preparation to a reaction solution (100 mM PBS buffer at pH 7.0, 100 mM sodium sulfite) containing 10% (w/v) eggshell membranes. The test enzyme preparation was any of BIOSORK, PROLEATHER FG-F, or PAPAIN W40, and added to give the final concentration of 0.5% (w/v). After the addition of the enzyme preparation, incubation was carried out at 37° C. for 12 hours under stirring, thereby completely solubilizing the eggshell membranes. As the control, a sample free from eggshell membrane and containing an enzyme preparation and a reducing agent was prepared.

The solubilized eggshell membranes thus obtained were subjected to heat treatment at 100° C. for 5 minutes (inactivation of protease), diluted 25 times with distilled water, and the ACE-inhibiting activity was measured using an ACE-inhibiting activity measurement kit "ACE Kit-WST" (Wako Pure Chemical Industries, Ltd.). This kit detects 3-hydroxybutyric acid (3HB) cut out from 3-hydroxybutyrylgLycyl-glycyl-glycine (3HB-GGG) by an enzyme method, and is simple and highly reproducible kit for measuring the ACE-inhibiting activity. The control value had been subtracted from the ACE-inhibiting activity of the solubilized eggshell membrane samples determined by the present method.

As shown in FIG. 27, it was found that the solubilized eggshell membranes have relatively high ACE-inhibiting ability. The inhibition rates were 72.4%, 74.5%, and 63.6% for the eggshell membranes solubilized with BIOSORK, PROLEATHER FG-F, and PAPAIN W40, respectively.

The above results indicate that the solubilized eggshell membranes obtained by the present method has ACE-inhibiting activity, and that the membranes have high utility value as a material having antihypertensive action.

INDUSTRIAL APPLICABILITY

According to the method of the present invention, eggshell membranes can be efficiently solubilized under mild conditions. More specifically, the method is highly advantageous in terms of the energy and material costs. In addition, the solubilized eggshell membranes obtained by the method of the present invention can be used in, for example, the medical field, food field, cosmetics (including skincare products), metal ion recovery, humectants, water absorbents, antibacterial substances, emulsifying agents, and hair growth tonics. It is also assumed that the solubilized eggshell membranes of the present invention are used to impart various effects (for example, antibacterial effect, water absorption and retention effect, rheology control effect, and cover protective effect). It is also expected that the solubilized eggshell membranes of the present invention are contained in a polymer material or the like, thereby improving the stretchability of the material.

The present invention will not be limited to the description of the embodiments and examples of the present invention. Various modifications readily made by those skilled in the art are also included in the present invention, without departing from the scope of claims. The contents of the articles, unexamined patent publications, and patent applications specified herein are hereby incorporated herein by reference.

The invention claimed is:

1. An eggshell membrane solubilization method which is able to completely solubilize eggshell membranes, comprising
    (a) contacting eggshell membranes with a protease and a reducing agent under mild conditions, wherein there is no washing step between the addition of the reducing agent and the addition of the protease, and
    (b) incubating the reaction of (a) for 10 minutes to 24 hours to achieve complete solubilization of the eggshell membranes,
    wherein the mild conditions are a pH from 6.0 to 9.5 and the concentration of the reducing agent is from 100 mM to 500 mM,
    wherein the protease is a serine endopeptidase,
    wherein the reducing agent is sulfite, a hydrogensulfite, L-cysteine, L-cysteine hydrochloride or N-acetyl-L-cysteine, and
    wherein the protease is subtilisin.

2. The eggshell membrane solubilization method of claim 1,
    wherein step (a) comprises the following steps (1) and (2):
    (1) providing eggshell membranes in a solvent; and
    (2) adding a reducing agent and a protease to the solvent, and causing reactions by them.

3. The eggshell membrane solubilization method of claim 1, wherein the reducing agent is sodium sulfite or sodium hydrogensulfite.

4. A method for extracting a useful component from eggshell membranes, comprising the following steps (i) and (ii):
    (i) completely solubilizing eggshell membrane according to the method of claim 1; and
    (ii) purifying the solubilized eggshell membranes obtained in step (i), thereby extracting a useful component.

5. The method of claim 4 for extracting a useful component from eggshell membranes, wherein the component purified in step (ii) is an enzyme selected from the group consisting of lysozyme and β-N-acetylglucosaminidase, or an acid mucopolysaccharide selected from the group consisting of hyaluronic acid, chondroitin sulfate, and dermatan sulfate.

6. The method of claim 1, wherein the reducing agent is not an acid.

7. The method of claim 2, wherein the reducing agent is not an acid.

8. The method of claim 1, wherein the protease concentration is between 0.01% and 1.0% (w/v).

9. The method of claim 1, wherein the period of time is 10 minutes to 12 hours.

10. The method of claim 1, wherein the period of time is about 60 minutes or less.

11. The eggshell membrane solubilization method of claim 1, wherein:
    the protease is one or more enzymes selected from alkaline serine endopeptidases; and
    the reducing agent is one or more reducing agents selected from the group consisting of sodium sulfite, sodium hydrogensulfite, L-cysteine and L-cysteine hydrochloride.

* * * * *